(12) United States Patent
Blokhin et al.

(10) Patent No.: US 10,059,681 B2
(45) Date of Patent: Aug. 28, 2018

(54) DISUBSTITUTED MALEIC ANHYDRIDES WITH ALTERED KINETICS OF RING CLOSURE

(71) Applicant: Arrowhead Madison Inc., Madison, WI (US)

(72) Inventors: Andrei V. Blokhin, Fitchburg, WI (US); David B. Rozema, Cross Plains, WI (US); Jonathan D. Benson, Stoughton, WI (US); Jeffrey C. Carlson, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 15/166,482

(22) Filed: May 27, 2016

(65) Prior Publication Data
US 2016/0272605 A1 Sep. 22, 2016

Related U.S. Application Data

(62) Division of application No. 14/119,074, filed as application No. PCT/US2012/040130 on May 31, 2012, now Pat. No. 9,481,661.

(60) Provisional application No. 61/498,025, filed on Jun. 17, 2011.

(51) Int. Cl.
| | |
|---|---|
| *C07D 307/66* | (2006.01) |
| *C07H 15/08* | (2006.01) |
| *C07H 15/26* | (2006.01) |
| *C07D 307/89* | (2006.01) |
| *C07D 307/60* | (2006.01) |
| *C07D 307/88* | (2006.01) |

(52) U.S. Cl.
CPC ......... *C07D 307/89* (2013.01); *C07D 307/60* (2013.01); *C07D 307/66* (2013.01); *C07D 307/88* (2013.01); *C07H 15/08* (2013.01); *C07H 15/26* (2013.01)

(58) Field of Classification Search
CPC ....... C07D 307/66; C07H 15/26; C07H 15/08
See application file for complete search history.

(56) References Cited

U.S. PATENT DOCUMENTS

| | | | |
|---|---|---|---|
| 4,017,299 | A | 4/1977 | Deihl et al. |
| 5,140,013 | A | 8/1992 | Gaudreault et al. |
| 6,525,031 | B2 | 2/2003 | Manoharan |
| 7,682,626 | B2 | 3/2010 | Rozema et al. |
| 2008/0152661 | A1 | 6/2008 | Rozema et al. |
| 2009/0048410 | A1 | 2/2009 | Wakefield et al. |
| 2011/0207799 | A1 | 8/2011 | Rozema et al. |

FOREIGN PATENT DOCUMENTS

| | | |
|---|---|---|
| WO | 2003100081 A2 | 12/2003 |
| WO | 2008022309 A2 | 2/2008 |

OTHER PUBLICATIONS

Fields et al., J. Org. Chem., 1990, 55, p. 5165-5170. (Year: 1990).*
Office Action for European Patent Application No. 12 801 275.4 dated Mar. 23, 2017.
Alder et al. "Dien-Synthesen mit Polyenen ω, ω'-Tetraphenyl-polyene und Maleinsäure-anhydrid", Justus Liebigs Annalen Der Chemie, vol. 570, No. 1, Oct. 12, 1950 (Oct. 12, 1950), pp. 178-190. p. 185; compound XXV.
Alder et al. "Die Konfiguration Der α-Und β-Eläostearinsäure", Justus Liebigs Annalen Der Chemie, vol. 609, No. 1, Oct. 11, 1957 (Oct. 11, 1957), pp. 19-39. p. 21; example VI.
Amarzguioui et al. "An algorithm for selection of functional siRNA sequences" Biochemical and Biophysical Research Communications 2004 vol. 316, p. 1050-1058.
Baag et al. "Synthesis of natural 3,4 cytotoxic camphorataimides Band C", Synthesis, Georg Thieme Verlag, Stuttgart, DE, No. 6, Mar. 11, 2006 (Mar. 11, 2006), pp. 1005-1008. p. 1006; compounds 10, 11.
Baenziger Ju et al. "Galactose and N-acetylgalactosamine-specific endocytosis of glycopeptides by isolated rat hepatocytes" Cell 1980 vol. 22, No. 2, p. 611-620.
Benoiton L, et al. Journal of the American Chemical Society 1959, vol. 81, p. 1726-17.
Chalk et al. "Improved and automated prediction of effective siRNA" Biochemical and Biophysical Research Communications 2004 vol. 319, p. 264-274.
Charlesworth et al. "Phthalide Formation: IV. Condensations with 5-Methoxy-3-Methylbenzoic Acid", Canadian Journal of Chemistry, vol. 41, No. 5, May 1, 1963 (May 1, 1963), pp. 1071-1077. compound XI.
International Search Report—corresponding application PCT/US212/40130.
Connolly et al. "Binding and endocytosis of cluster glycosides by rabbit hepatocytes. Evidence for a short-circuit pathway that does not lead to degradation" Journal of Biological Chemistry 1982 vol. 257, No. 2, p. 939-945.
D'Alelio et al. "Reactions of Furan Compounds. XIX. Synthesis of 2-Methoxyfuran and its 5-Methyl- and 5-Methoxymethyl Derivatives", The Journal of Organic Chemistry, vol. 25, No. 6, Jun. 1, 1960 (Jun. 1, 1960), pp. 1028-1030. p. 1029; compound IV.
Dyakonov et al. "Remarks about the paper Synthesis of cyclopropene derivatives by the D'yakonov reaction by Breslow and Chipman", Zhurnal Obshchei Khimii, Nauka, Russia, vol. 31, Jan. 1, 1961 (Jan. 1, 1961), pp. 3483-3485. p. 3483; compound 6.
Eberson et al. J. Am. Chem. Soc. 1971, vol. 93, No. 22, p. 5821-5826.
Fang et al. "Use of α-anilino dienenitriles as nucleophiles in cycloadditions", The Journal of Organic Chemistry, American Chemical Society, US, vol. 54, No. 2, Jan. 1, 1989 (Jan. 1, 1989), pp. 477-481. p. 478; compounds 8-10.

(Continued)

*Primary Examiner* — Jonathan S Lau
(74) *Attorney, Agent, or Firm* — Robert Michael Teigen

(57) ABSTRACT

We describe anhydride compounds suitable for physiologically labile modification of amine-containing molecules. The described anhydrides form reversible linkages having desirable kinetics for in vivo delivery of biologically active molecules. Also described are endosomolytic polymers formed by modification of membrane active polyamines with the described anhydrides.

7 Claims, No Drawings

(56) References Cited

OTHER PUBLICATIONS

Fang et al. Cycloadditions of of α-Aminontrile Diene: Journal of the Chemical Society, Chemical Communications, No. 19, Jan. 1, 1985 (Jan. 1, 1985), p. 1356-1357.

Heale et al. "siRNA target site secondary structure predictions using local stable substructures" Nucleic Acids Research 2005, vol. 33, No. 3.

Iobst ST et al. "Selective Sugar Binding to the Carbohydrate Recognition Domains of the Rat Hepatic and Macrophage Asialoglycoprotein Receptors." Journal of Biological Chemistry (1996) 271(12), p. 6686-6693.

Khvorova et al. "Functional siRNAs and miRNAs Exhibit Strand Bias" Cell 2003 vol. 115, p. 209-216.

Kirby AJ "Effective Molarities for Intramolecular Reactions" Adv. Phys. Org. Chem. 1980 p. 183-278.

Kirby et al. J Chem Soc., Perkin Trans. 2, 1972, 1206-1214.

Leonard et al. Synthesis 2000, vol. 4, 507-509.

Malhotra M et al. "A novel method for synthesizing PEGylated chitosan nanoparticles: strategy, preparation, and in vitro analysis" International Journal of Nanomedicine 2011 vol. 6, p. 485-494.

McCulloch et al. "Influence of Lewis acids on the Diels-Alder reaction. II. Rearrangement of 1- and 1,4-substituted diethyl 7-oxabicyclo[2-2-1]2,5-heptadiene-2,3-dica riboxylate adducts to 4- and 4,6-substituted diethyl 3-hydroxyphthalates" Canadian Journal of Chemistry, vol. 47, No. 23, Dec. 1, 1969 (Dec. 1, 1969), pp. 4319-4326. p. 4323; compounds 4b, d-i.

Pei et al. "On the art of identifying effective and specific siRNAs" Nature Methods 2006 vol. 3, No. 9, p. 670-676.

Pillai et al. "Repression of protein synthesis by miRNAs: how many mechanisms?" Trends in Cell Biology 2007 vol. 17(3), p. 118-126.

Prakash et al. "Choice of a structure for internal anhydride of 3-methylcyclothex-1-ene-1,2,3-tricarboxylic acid—application of UV absorption characteristics of 1,2-enedioic anhydrides", Indian Journal of Chemistry. Section B, Council of Scientific and Industrial Research (CS I R), IN, vol. 19, No. 7, Jul. 1, 1980 (Jul. 1, 1980), pp. 601-602. p. 601; compounds 4, 7.

Reynolds et al. "Targeting the cancer stroma with a fibroblast activation protein-activated promelittin protoxin" Nature Biotechnology 2004 vol. 22(3), p. 326-30.

Rozema et al. "Dynamic PolyConjugates for targeted in vivo delivery of siRNA to hepatocytes" Proc. Natl. Acad. Sci. USA, 2007, vol. 104, No. 32, p. 12982-12987.

Sato M, et al. Bulletin of the Chemical Society of Japan 1959, vol. 32, p. 203-204.

Sato M, et al. "A new synthesis of threonine" Bulletin of the Chemical Society of Japan 1959, vol. 30, No. 9 p. 937-938.

Scarpa et al. "Zur kenntnis des Fuerstions; Synthesen alkylsubstituierter Phtalsäuren", Helvetica Chimica Acta, vol. 49, No. 2, Mar. 10, 1966 (Mar. 10, 1966), pp. 858-870.

Schottelius et al. "Rapid 3,5,6 Synthesis of α,β-Didehydroaspartic-Acid Derivatives Carrying a β-Substituent", Helvetica Chimica Acta, vol. 81, No. 12, Dec. 16, 1998 (Dec. 16, 1998), pp. 2341-2347.

Schwarz et al. "Asymmetry in the Assembly of the RNAi Enzyme Complex" Cell 2003 vol. 115, p. 199-208.

Semmelhack et al. "Reaction of (aminocarbene)iron complexes with alkynes. A synthesis of 5-aminofurans", Organometallics, vol. 5, No. 12, Dec. 1, 1986 (Dec. 1, 1986), pp. 2550-2552. p. 2552; compound 23.

Spino C et al. "Characteristics of the tor frontier orbital interactions in the Diels-Alder cycloaddition" Journal of Organic Chemistry 2004, vol. 69, p. 757-764.

Ui-Tei et al. "Guidelines for the selection of highly effective siRNA sequences for mammalian and chick RNA interference" Nucleic Acids Research 2004 vol. 32(3)936-948.

Wingert et al. "Synthesen mit Cyclobutadienen, 10. Sterische Einflüsse auf Isomerisierungen im System Dewarbenzol/Benzol/Prisman", Chemische Berichte, vol. 119, No. 1, Jan. 1, 1986 (Jan. 1, 1986), pp. 244-256. p. 250; compounds 12a, 12b.

Supplementary European Search Report for corresponding European Application No. EP 12 80 1275 dated Apr. 29, 2015.

Search Opinion for corresponding European Application No. EP 12 80 1275.

Office Action for European Patent Application No. 12 801 275.4 dated Jun. 15, 2016.

* cited by examiner

DISUBSTITUTED MALEIC ANHYDRIDES WITH ALTERED KINETICS OF RING CLOSURE

PRIORITY

The present application is a division of U.S. patent application Ser. No. 14/119,074, filed Jan. 8, 2014, now U.S. Pat. No. 9,481,661, which is a U.S. National Phase Application under 35 U.S.C. § 371 of International Patent Application No. PCT/US2012/040130, filed on May 31, 2012, which claims the benefit of U.S. Provisional Patent Application No. 61/498,025, filed June 17, 2011, the contents of each of which are incorporated herein in their entirety.

BACKGROUND OF THE INVENTION

Maleic anhydrides are used in medicinal and formulation chemistry for labile covalent linkage between molecules of interest. Introduction of alkyl substituents at positions 2 and 3 of maleic anhydride shifts equilibrium of reaction with aliphatic amines towards free amine and maleic anhydride at pH<7.

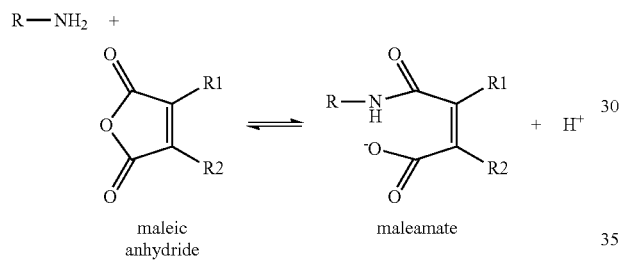

At pH >7, the reaction is driven toward the maleamate (maleamic acid when carboxyl group is protonated). At acidic pH, the reaction is driven towards the anhydride and the free amine. This property is useful because in mammals, the pH of blood is about 7.4 (slightly alkaline) while certain intracellular compartments, such as endosomes and lysosome, are acidic (pH<6).

The rate of conversion of maleamates to amines and maleic anhydrides is strongly dependent on substitution at positions 2 and 3 (R1 and R2) of the maleic anhydride system. When R1 and R2 are both hydrogen (maleic anhydride) the reaction is nearly irreversible. Substitution of a single alkyl group at position R1 or R2 (e.g., citraconic anhydride) increases the rate of the reverse reaction 50-fold higher compared to maleic anhydride. At pH 5, the half life for cleavage of a mono-substituted maleamate to yield the free amine and the anhydride is about 8 to 24 h. This half-life is too slow for delivery systems where rapid lability is important. For disubstituted maleamates, steric repulsion of the 2,3 aliphatic groups drives the reaction toward ring closure to form the anhydride and free amine (Kirby Adv. Phys. Org. Chem. 1980, 17, 183-278; Kirby et al. J Chem Soc., Perkin Trans. 2, 1972, 1206-1214). Alkyl substitutions at both R1 and R2 (e.g., 2,3-dimethylmaleic anhydride) increase the rate of the reverse reaction 10,000-fold compared to maleic anhydride. Half-life of cleavage of a disubstituted maleamate from a polyamine is about 5 min at 37° C. and pH 5.5.

The reverse reaction for 2-propionic-3-methylmaleamic acid has been observed to be the same as that for 2,3-dimethylmaleamic acid. We have previously described the use of 2-propionic-3-methylmaleic anhydride (CDM) derivatives for reversible modification of amine-containing polymers (Rozema et al. Proc. Natl. Acad. Sci. USA, 2007, Vol. 104, No. 32, p. 12982-12966). However, the half-life for dialkyl-substituted maleamates can be too energetically favorable, i.e. amide cleavage can occur too rapidly even near neutral pH, for certain in vivo labile delivery systems. At pH 7.5 and 37° C., cleavage of the amide bond in 2,3-dialkyl maleamates to yield anhydrides and free amines occurs with a $t_{1/2}$ of about 4 h. This rate is too rapid for applications in which longer circulation time is desired. Thus, there is a need for physiologically labile bonds which are more stable in circulation yet retain rapid reversibility in the pH 6 environment of a cell endosome.

It has been shown that connecting alkyl substitutions into a cycle decreases the rate of ring closure reaction in 2,3-dialkyl maleamate. For example, amine release from mono N-methylamido derivative formed from 4,5,6,7-terahydrobenzo[c]furan-1,3-dione and methylamine has $k_{obs}=3.5 \times 10^{-2}$ (Kirby Adv. Phys. Org. Chem. 1980, 17, 183-278), is 17.5 times faster than for respective 2-methylmaleamate and 32 times slower than for 2,3-dimethylmaleamate. For benzo [c]furan-1,3-dione, introduction of alkyl groups at positions 4 and 7 shifts equilibrium in water toward ring closure. $K=k_1/k_{-1}$ in this equilibrium is 1.5, compare with K=5.3 for the same equilibrium measured for dimethyl maleic acid, or $K=10^{-2}$ for phthalic acid itself (Eberson et al. J. Am. Chem. Soc. 1971, Vol. 93, No. 22, p. 5821-5826).

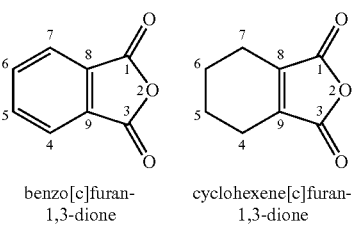

benzo[c]furan-1,3-dione     cyclohexene[c]furan-1,3-dione

We describe here new disubstituted maleic anhydrides which yield maleamates having half-lives that are shorter than mono-substituted maleamates but slower than previously described dialkyl-substituted maleamates. These new anhydrides, with their slower rate of amide cleavage, achieve longer circulation times in vivo and extended shelf life relative to formulations using previously described disubstituted maleic anhydrides.

SUMMARY OF THE INVENTION

In a preferred embodiment, we describe a class of maleic anhydride derivatives having a cyclohexene or benzene ring fused to the c-side of the maleic anhydride (2,5-furandione) ring: benzo[c]furan-1,3-diones (phthalic acid anhydrides) and cyclohexene[c]furan-1,3-diones.

In one embodiment, we describe modified cyclohexene [c]furan-1,3-diones, CycHex-CDM, having the structure:

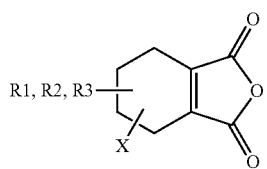

wherein X is —(CH$_2$)$_n$—Z,

Z is a carboxyl group, ester group, amide group, ether group, tertiary amine group, or protected amine group, or Z may comprise a targeting group as defined herein or a steric stabilizer group as defined herein, and n is an integer from 0-8; and, R1, R2, and R3 are independently selected from hydrogen, aliphatic group, and aromatic group.

In one embodiment, we describe membrane active polyamines reversibly modified by reaction with the above described CycHex-CDM, having the structure:

wherein X, R1, R2, and R3 are as described above. In a preferred embodiment, X comprises a targeting group. A preferred targeting group is an N-acetylgalactosamine. In another preferred embodiment, X comprises a steric stabilizer. A preferred steric stabilizer is a polyethyleneglycol (PEG). In yet another preferred embodiment, a plurality of maleic anhydrides of the invention are linked to a single polyamine. In yet another preferred embodiment, the reversibly modified membrane active polyamine in not membrane active. Cleavage of the anhydrides from the modified polymer, such as in response to a decrease in pH, restores amines, and thereby membrane activity, to the membrane active polyamine.

In another embodiment, we describe 4,7-disubstituted benzo[c]furan-1,3-dione (Benzo-CDM), having the structure:

wherein X is —(CH$_2$)$_n$—Z,

Z is a carboxyl group, ester group, amide group, ether group, tertiary amine group, or protected amine group, or Z may comprise a targeting group as defined herein or a steric stabilizer group as defined herein, and n is an integer from 0-8; and, R1, R2, and R3 are independently selected from hydrogen, aliphatic group, and aromatic group, and m is an integer from 1-8.

In one embodiment, we describe membrane active polyamines reversibly modified by reaction with the above described Benzo-CDM having the structure:

wherein X, R1, R2, R3, and m are as described above. In a preferred embodiment, X comprises a targeting group. A preferred targeting group is an N-acetylgalactosamine. In another preferred embodiment, X comprises a steric stabilizer. A preferred steric stabilizer is a PEG. In yet another preferred embodiment, a plurality of maleic anhydrides of the invention are linked to a single polyamine. In yet another preferred embodiment, the reversibly modified membrane active polyamine is not membrane active. Cleavage of the anhydrides from the modified polymer, such as in response to a decrease in pH, restores amines, and thereby membrane activity, to the membrane active polyamine.

In a preferred embodiment, we describe disubstituted maleic anhydrides in which one of the substitutions contains an electron withdrawing group (EWG). Electron withdrawing groups draw electrons away from a reaction center. By placing an electron withdrawing group at position C2 or C3 of the anhydride, the pKa of the anhydride constituent carboxylic acid is reduced. Thus, introduction of electron withdrawing groups (EWG) into maleamates increases acidity of the carboxyl group thereby decreasing the rate of the ring closure reaction.

In one embodiment, we describe 4-Ar-furan-1,3-dione derivatives (Ar-CDM) having the structure:

wherein X is —(CH$_2$)$_n$—Z,

Z is a carboxyl group, ester group, amide group, ether group, tertiary amine group, or protected amine group, or Z may comprise a targeting group as defined herein or a steric stabilizer group as defined herein, and n is an integer from 0-8; and, R1 is an aliphatic group or aromatic group.

In one embodiment, we describe membrane active polyamines reversibly modified by reaction with the above described Ar-CDM, having the structure:

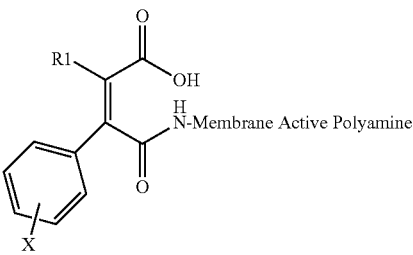

wherein X and R1 are as described above. In a preferred embodiment, X comprises a targeting group. A preferred targeting group is an N-acetylgalactosamine. In another preferred embodiment, X comprises a steric stabilizer. A preferred steric stabilizer is a PEG. In yet another preferred embodiment, a plurality of maleic anhydrides of the invention are linked to a single polyamine. In yet another preferred embodiment, the reversibly modified membrane active polyamine is not membrane active. Cleavage of the anhydrides from the modified polymer, such as in response to a decrease in pH, restores amines, and thereby membrane activity, to the membrane active polyamine.

In another embodiment, we describe 4-alkoxy-furan-1,3-dione derivatives (Alkoxy-CDM) having the structure:

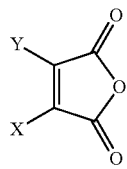

wherein X is —$(CH_2)_n$—Z,
Z is a carboxyl group, ester group, amide group, ether group, tertiary amine group, or protected amine group, or Z may comprise a targeting group as defined herein or a steric stabilizer group as defined herein, and
n is an integer 0-8;
Y is —$CH_2$—O—R1 or —NH—CO—R1; and
R1 is an aliphatic group.

In one embodiment, we describe membrane active polyamines reversibly modified by reaction with the above described Alkoxy-CDM, having the structure:

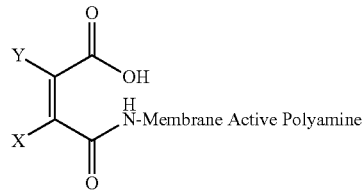

wherein X, M, and Y are as described above. In a preferred embodiment, X comprises a targeting group. A preferred targeting group is an N-acetylgalactosamine. In another preferred embodiment, X comprises a steric stabilizer. A preferred steric stabilizer is a PEG. In yet another preferred embodiment, a plurality of maleic anhydrides of the invention are linked to a single polyamine. In yet another preferred embodiment, the reversibly modified membrane active polyamine is not membrane active. Cleavage of the anhydrides from the modified polymer, such as in response to a decrease in pH, restores amines, and thereby membrane activity, to the membrane active polyamine.

In another embodiment, we describe 4-alkoxy-furan-1,3-dione derivatives (Alkoxy-CDM) having the structure:

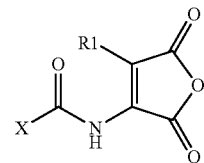

wherein X is —$(CH_2)_n$—Z,
Z is a hydroxyl group or Z may comprise a targeting group as defined herein or a steric stabilizer group as defined herein, and
n is an integer 0-8;
R1 is an aliphatic group.

In one embodiment, we describe membrane active polyamines reversibly modified by reaction with the above described Alkoxy-CDM, having the structure:

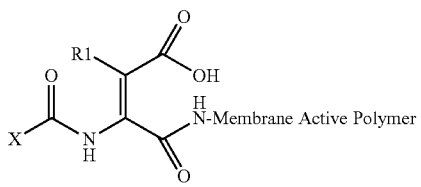

wherein X, and R1 are as described above. In a preferred embodiment, X comprises a targeting group. A preferred targeting group is an N-acetylgalactosamine. In another preferred embodiment, X comprises a steric stabilizer. A preferred steric stabilizer is a PEG. In yet another preferred embodiment, a plurality of maleic anhydrides of the invention are linked to a single polyamine. In yet another preferred embodiment, the reversibly modified membrane active polyamine is not membrane active. Cleavage of the anhydrides from the modified polymer, such as in response to a decrease in pH, restores amines, and thereby membrane activity, to the membrane active polyamine.

The disubstituted maleic anhydrides described above may be use to reversibly link a molecule of interest to an amine containing compound. The molecule of interest may be at position R1, R2, R3, or Z of any of the above described anhydrides. The molecule of interest may be selected from the group comprising: active pharmaceutical ingredient (API), small molecule drug, nucleic acid, interaction modifier, targeting group, or delivery agent. Preferably, the molecule of interest does not itself contain a free amine.

In another preferred embodiment, the invention features a composition for delivering a polynucleotide to a cell in vivo comprising a reversibly modified membrane active polymer as described above reversibly conjugated to a polynucleotide via a physiologically labile linkage. The physiologically labile linkage to the polynucleotide may be cleaved under the same or different conditions than the maleamate linkages. The polynucleotide-polymer conjugate is administered to a mammal in a pharmaceutically acceptable carrier or diluent.

Further objects, features, and advantages of the invention will be apparent from the following detailed description when taken in conjunction with the accompanying drawings.

DETAILED DESCRIPTION OF THE INVENTION

The present invention is directed to compounds, compositions, and methods useful for reversibly modifying membrane active polymers. The reversibly modified polymers are suitable for delivering polynucleotides or other cell-impermeable molecules to mammalian cells. The compounds comprise disubstituted maleic anhydride derivatives having desirable kinetics of ring closure in physiological conditions. As shown in the reaction above, anhydrides are able to react with anime groups in aqueous solution in a reaction that is reversible. Reaction of a disubstituted maleic anhydride derivative with an amine yields a maleamate. The maleamate is pH labile. At acidic pH, the maleamate amide bond is cleaved, yielding a cyclic anhydride and the amine. Thus, disubstituted maleic anhydride derivatives provide a means to reversibly link a molecule of interest, such as a small molecule, targeting group, steric stabilizer, or nucleic acid to an amine-containing compound, such as a membrane active polyamine, via a physiologically labile linkage.

CycHex-CDM compounds of the invention have the structure:

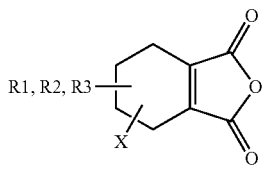

wherein X is —$(CH_2)_n$—Z,
Z is a carboxyl group, ester group, amide group, ether group, tertiary amine group, or protected amine group, or Z may comprise a targeting group as defined herein or a steric stabilizer group as defined herein, and n is an integer from 0-8; and,
R1, R2, and R3 are independently selected from hydrogen, aliphatic group, and aromatic group.
Z is selected to contain a molecule of interest, such as a targeting group or a steric stabilizer, or to be a reactive group which can be used to attach the molecule of interest.

Benzo-CDM compounds of the invention have the structure:

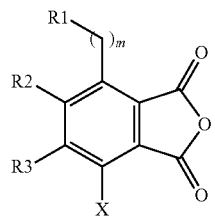

wherein X is —$(CH_2)_n$—Z,
Z is a carboxyl group, ester group, amide group, ether group, tertiary amine group, or protected amine group, or Z may comprise a targeting group as defined herein or a steric stabilizer group as defined herein, and n is an integer from 0-8; and,
R1, R2, and R3 are independently selected from hydrogen, aliphatic group and aromatic group, and m is an integer from 1-8.
Z is selected to contain a molecule of interest, such as a targeting group or a steric stabilizer, or to be a reactive group which can be used to attach the molecule of interest.

Ar-CDM compounds of the invention have the structure:

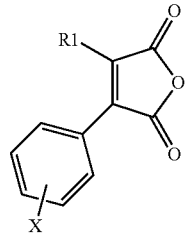

wherein X is —$(CH_2)_n$—Z,
Z is a carboxyl group, ester group, amide group, ether group, tertiary amine group, or protected amine group, or Z may comprise a targeting group as defined herein or a steric stabilizer group as defined herein, and n is an integer 0-8; and,
R1 is an aliphatic group or aromatic group.
Z is selected to contain a molecule of interest, such as a targeting group or a steric stabilizer, or to be a reactive group which can be used to attach the molecule of interest.

Alkoxy-CDM compounds of the invention have the structure:

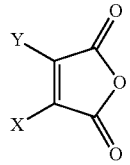

wherein X is —$(CH_2)_n$—Z,
Z is carboxyl group, ester group, amide group, ether group, tertiary amine group, or protected amine group, or Z may comprise a targeting group as defined herein or a steric stabilizer group as defined herein, and n is an integer 0-8;
Y is —$CH_2$—O—R1 or —NH—CO—R1; and
R1 is an aliphatic group.
Z is selected to contain a molecule of interest, such as a targeting group or a steric stabilizer, or to be a reactive group which can be use to attach the molecule of interest.

Amido-CDM compounds of the invention have the structure:

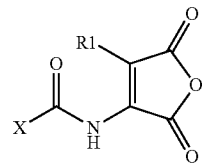

wherein X is —$(CH_2)_n$—Z,
Z is a hydroxyl group or Z may comprise a targeting group as defined herein or a steric stabilizer group as defined herein, and
n is an integer 0-8;
R1 is an aliphatic group.

Z is selected to contain a molecule of interest, such as a targeting group or a steric stabilizer, or to be a reactive group which can be use to attach the molecule of interest.

Each of the above compounds, CycHex-CDM, Benzo-CDM, Ar-CDM, and Alkoxy-CDM react with amines to yield physiologically labile maleamate linkages. In particular, the compounds of the invention are particularly suitable for reversible modification of membrane active polymers as described in U.S. Patent Publications 2008-0152661 and U.S. patent application Ser. No. 13/032,029 (each of which is incorporated herein by reference)

A linkage or linker is a connection between two atoms that links one chemical group or segment of interest to another chemical group or segment of interest via one or more covalent bonds. For example, a linkage can connect a molecule of interest to a polymer. A reversible or labile linkage contains a reversible or labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides. Spacer groups are well known in the art and the preceding list is not meant to limit the scope of the invention.

A labile bond is a covalent bond other than a covalent bond to a hydrogen atom that is capable of being selectively broken or cleaved under conditions that will not break or cleave other covalent bonds in the same molecule. More specifically, a labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life ($t_{1/2}$) of bond cleavage (the time required for half of the bonds to cleave). Thus, reversible or labile bonds encompass bonds that can be selectively cleaved more rapidly than other bonds in a molecule.

Appropriate conditions are determined by the type of labile bond and are well known in organic chemistry. Labile bonds of maleamates as disclosed herein are pH sensitive. Cleavage of the maleamate linkage is accelerated in acidic pH.

As used herein, a physiologically labile bond is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes.

Reversible modification of a membrane active polyamine with the described disubstituted maleic anhydride compounds reduces non-productive serum and non-target cell interactions and reduces toxicity of the polyamine in vivo. Further utility is gained by using the described disubstituted maleic anhydride compounds to reversibly attach targeting ligands and steric stabilizers to the membrane active polyamines. Reversible modification to attach targeting groups and/or steric stabilizers enhance cell-specific binding and endocytosis, shield the polymer from non-specific interactions, increase circulation time, enhance specific interactions, inhibit toxicity, or alter the charge of the polymer. The described physiologically labile disubstituted maleamates maintain sufficient stability in the pH 7.4 environment of the blood, but are readily cleaved from the polyamine, thereby unmasking the polyamine and restoring activity of the unmasked polyamine in the reduced pH environment of the cellular endosome/lysosome.

As used herein, membrane active polymers are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polymer's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Polymers that preferentially cause disruption of endosomes or lysosomes over plasma membrane are considered endosomolytic. The effect of membrane active polymers on a cell membrane may be transient. Membrane active polymers possess affinity for the membrane and cause a denaturation or deformation of bilayer structures. Membrane active polymers may be synthetic or non-natural amphipathic polymers.

As used herein, membrane active polymers are distinct from a class of polymers termed cell penetrating peptides or polymers represented by compounds such as the arginine-rich peptide derived from the HIV TAT protein, the antennapedia peptide, VP22 peptide, transportan, arginine-rich artificial peptides, small guanidinium-rich artificial polymers and the like. While cell penetrating compounds appear to transport some molecules across a membrane, from one side of a lipid bilayer to other side of the lipid bilayer, apparently without requiring endocytosis and without disturbing the integrity of the membrane, their mechanism is not understood.

Delivery of a polynucleotide to a cell is mediated by the membrane active polymer disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Endosomolytic polymers are polymers that, in response to an endosomal-specific environmental factor, such as reduced pH or the presence of lytic enzymes, are able to cause disruption or lysis of an endosome or provide for release of a normally cell membrane impermeable compound, such as a polynucleotide or protein, from a cellular internal membrane-enclosed vesicle, such as an endosome or lysosome. Endosomolytic polymers undergo a shift in their physico-chemical properties in the endosome. This shift can be a change in the polymer's solubility or ability to interact with other compounds or membranes as a result of a shift in charge, hydrophobicity, or hydrophilicity. Exemplary endosomolytic polymers have pH-labile groups or bonds. A reversibly masked membrane active polymer, wherein the masking agents are attached to the polymer via pH labile bonds, can therefore be considered to be an endosomolytic polymer.

Modification of the membrane active polymer can be done to reversibly inhibit, or mask, the polymer and to provide cell or tissue targeting properties. Modification using the described anhydrides also neutralizes the polyamine to reduce positive charge and form a near neutral charged polymer.

The membrane active polyamines of the invention are capable of disrupting plasma membranes or lysosomal/endocytic membranes. This membrane activity is an essential feature for cellular delivery of the polynucleotide. Unmodified membrane active polymers, however, are potentially toxic when administered in vivo. Polyamines also interact readily with many anionic components in vivo, leading to undesired bio-distribution. Therefore, reversible masking of membrane activity of the polyamine is necessary for in vivo use. This masking is accomplished through reversible attachment of masking agents to the membrane active polyamine to form a reversibly masked membrane active polymer, i.e. a delivery polymer. In addition to inhibiting membrane activity, the masking agents shield the polymer from non-specific interactions, reduce serum interactions, increase circulation time, and provide cell-specific interactions, i.e. targeting.

Masking agents, in aggregate, may inhibit membrane activity of the polymer and provide in vivo hepatocyte targeting. Masking agents may also shield the polymer from non-specific interactions (reduce serum interactions, increase circulation time). The membrane active polyamine is membrane active in the unmodified (unmasked) state and not membrane active (inactivated) in the modified (masked) state. A sufficient number of masking agents are linked to the polymer to achieve the desired level of inactivation. The desired level of modification of a polymer by attachment of masking agent(s) is readily determined using appropriate polymer activity assays. For example, if the polymer possesses membrane activity in a given assay, a sufficient level of masking agent is linked to the polymer to achieve the desired level of inhibition of membrane activity in that assay. Masking requires modification of $\geq 50\%$, $\geq 60\%$, $\geq 70\%$, $\geq 80\%$ or $\geq 90\%$ of the primary amine groups on a population of polymer, as determined by the quantity of primary amines on the polymer in the absence of any masking agents. It is also a preferred characteristic of masking agents that their attachment to the polymer reduces positive charge of the polymer, thus forming a more neutral delivery polymer. It is desirable that the masked polymer retain aqueous solubility. Masking with PEGs also helps in prevention of aggregation of electrically neutral polymers which can result in formation of large particles.

As used herein, a membrane active polyamine is masked if the modified polymer does not exhibit membrane activity and exhibits cell-specific (i.e. hepatocyte) targeting in vivo. A membrane active polyamine is reversibly masked if cleavage of bonds linking the masking agents to the polymer results in restoration of amines on the polymer thereby restoring membrane activity.

As used herein, a masking agent comprises a disubstituted maleic anhydride compound of the invention having an targeting moiety (or group) or a steric stabilizer at position Z. A preferred targeting moiety is an ASGPr targeting moiety. An ASGPr targeting moiety is a group, typically a saccharide, having affinity for the asialoglycoprotein receptor. A preferred steric stabilizer is a polyethylene glycol (PEG). The membrane active polyamine can be conjugated to masking agents in the presence of an excess of masking agents. The excess masking agent may be removed from the conjugated delivery polymer prior to administration of the delivery polymer.

As used herein, a targeting group is a ligand having affinity for a cell surface receptor. Targeting moieties or groups enhance the pharmacokinetic or biodistribution properties of a conjugate to which they are attached to improve cell-specific distribution and cell-specific uptake of the conjugate. Preferred targeting groups contain saccharides having affinity for the ASGPr, including but not limited to: galactose, N-Acetyl-galactosamine and galactose derivatives. Galactose derivatives having affinity for the ASGPr are well known in the art. A variety of ligands have been used to target drugs and genes to cells and to specific cellular receptors. Cell receptor ligands may be selected from the group comprising: carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin). Examples of targeting groups include those that target the asialoglycoprotein receptor by using asialoglycoproteins or galactose residues. For example, liver hepatocytes contain ASGP Receptors. Therefore, galactose-containing targeting groups may be used to target hepatocytes. Galactose containing targeting groups include, but are not limited to: galactose, N-acetylgalactosamine, oligosaccharides, and saccharide clusters (such as: Tyr-Glu-Glu-(aminohexyl Gal-NAc)$_3$, lysine-based galactose clusters, and cholane-based galactose clusters). Further suitable conjugates can include oligosaccharides that can bind to carbohydrate recognition domains (CRD) found on the asialoglycoprotein-receptor (ASGP-R). Example conjugate moieties containing oligosaccharides and/or carbohydrate complexes are provided in U.S. Pat. No. 6,525,031.

Galactose and galactose derivates have been used to target molecules to hepatocytes in vivo through their binding to the asialoglycoprotein receptor (ASGPr) expressed on the surface of hepatocytes. As used herein, a ASGPr targeting moiety comprises a galactose and galactose derivative having affinity for the ASGPr equal to or greater than that of galactose. Binding of galactose targeting moieties to the ASGPr(s) facilitates cell-specific targeting of the delivery polymer to hepatocytes and endocytosis of the delivery polymer into hepatocytes. ASGPr targeting moieties may be selected from the group comprising: lactose, galactose, N-acetylgalactosamine (GalNAc, NAG), galactosamine, N-formylgalactosamine, N-acetylgalactosamine, N-propionylgalactosamine, N-n-butanoylgalactosamine, and N-isobutanoylgalactosamine (Iobst, S. T. and Drickamer, K. *J.B.C.* 1996, 271, 6686). ASGPr targeting moieties can be monomeric (e.g., having a single galactosamine) or multimeric (e.g., having multiple galactosamines) (Baenziger and Fiete, 1980, Cell, 22, 611-620; Connolly et al., 1982, J. Biol. Chem., 257, 939-945).

As used herein, a steric stabilizer is a non-ionic hydrophilic polymer (either natural, synthetic, or non-natural) that prevents or inhibits intramolecular or intermolecular interactions of a polymer to which it is attached relative to the polymer containing no steric stabilizer. A steric stabilizer hinders a polymer to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a polymer. A preferred steric stabilizer is a polyethylene glycol (PEG) or PEG derivative. As used herein, a preferred PEG can have about 1-500 ethylene glycol monomers, 2-20 ethylene glycol monomers, 5-15 ethylene glycol monomers, or about 10 ethylene glycol monomers. As used herein, a preferred PEG can also have a molecular weight average of about 85-20,000 Daltons (Da), about 200-1000 Da, about 200-750 Da, or about 550 Da. As used herein, steric stabilizers prevent or inhibit intramolecular or intermolecular interactions of a polymer to which it is attached relative to the polymer containing no steric stabilizer in aqueous solution.

In one embodiment, the membrane active polyamine is reversibly masked by attachment of ASGPr targeting moiety masking agents to ≥50%, ≥60%, ≥70%, ≥80%, or ≥90% of primary amines on the polyamine. In another embodiment, the membrane active polyamine is reversibly masked by attachment of ASGPr targeting moiety masking agents and PEG masking agents to ≥50%, ≥60%, ≥70%, ≥80%, or ≥90% of primary amines on the polymer. When both ASGPr targeting moiety masking agents and PEG masking agents, a ratio of PEG to ASGPr targeting moiety is about 0-4:1, more preferably about 0.5-2:1.

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap moiety at the 5' end, the 3' end, or both the 5' and 3' ends. The cap moiety can be, but is not limited to, an inverted deoxy abasic moiety, an inverted deoxy thymidine moiety, a thymidine moiety, or 3' glyceryl modification.

An RNA interference (RNAi) polynucleotide is a molecule capable of inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). RNAi polynucleotides may be selected from the group comprising: siRNA, microRNA, double-strand RNA (dsRNA), short hairpin RNA (shRNA), and expression cassettes encoding RNA capable of inducing RNA interference. siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The term "small molecule" as used herein, refers to organic or inorganic molecules either synthesized or found in nature, generally having a molecular weight less than 10,000 grams per mole, optionally less than 5,000 grams per mole, and optionally less than 2,000 grams per mole.

As used herein, an "aliphatic group" is a univalent group derived from an aliphatic compound by removal of a hydrogen atom from a carbon atom. An aliphatic compound is an acyclic or cyclic, saturated or unsaturated carbon compound, excluding aromatic compounds, in which carbon atoms are joined together in straight chains, branched chains, or non-aromatic rings. Also as used herein, elements other than hydrogen can be bound to the carbon chain including, but not limited to: oxygen, nitrogen, sulfur, and chlorine.

As used herein, in vivo means that which takes place inside an organism and more specifically to a process performed in or on the living tissue of a whole, living multicellular organism (animal), such as a mammal, as opposed to a partial or dead one.

A conjugate of the present invention can be administered by a variety of methods known in the art. As will be appreciated by the skilled artisan, the route and/or mode of administration will vary depending upon the desired results. To administer a conjugate of the invention by certain routes of administration, it may be necessary to coat the conjugate with, or co-administer the conjugate with, a material to prevent its inactivation. For example, the conjugate may be administered to a subject in an appropriate carrier or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

A carrier may also contain adjuvants such as preservatives, wetting agents, emulsifying agents, and dispersing agents. Prevention of the presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions of the invention. The compounds of the present invention can be administered via any suitable route, most preferably parenterally, in a preparation appropriately tailored to that route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

The phrases "parenteral administration" and "administered parenterally" as used herein means modes of administration other than enteral and topical administration, usually by injection, and includes, without limitation: intravascular, intravenous, intraarterial, intramuscular, intraparenchymal, intratumoral, intrathecal, intracapsular, intraorbital, intracardiac, intraperitoneal, transtracheal, subcutaneous, subdermal, subcuticular, intraarticular, subcapsular, subarachnoid, intraspinal, subdural, epidural, intrathecal, intralymphatic, and intrasternal injection and infusion.

Regardless of the route of administration selected, the conjugates of the present invention, which may be used in a suitable hydrated form, and/or the pharmaceutical compositions of the present invention, are formulated into pharmaceutically acceptable dosage forms by conventional methods known to those of skill in the art.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals and more particularly in humans. As used herein, "pharmaceutical composition" includes the conjugates of the invention, a pharmaceutical carrier or diluent and any other media or agent necessary for formulation. As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

RNAi polynucleotides may be delivered for research purposes or to produce a change in a cell that is therapeutic. In vivo delivery of RNAi polynucleotides is useful for research reagents and for a variety of therapeutic, diagnostic, target validation, genomic discovery, genetic engineering, and pharmacogenomic applications. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease. A person having ordinary skill in the art of gene therapy would reasonably anticipate beneficial levels of expression of a gene specific for a disease based upon sufficient levels of marker gene results.

EXAMPLES

Example 1

Cyclohexene-CDM (CycHex-CDM) Derivative

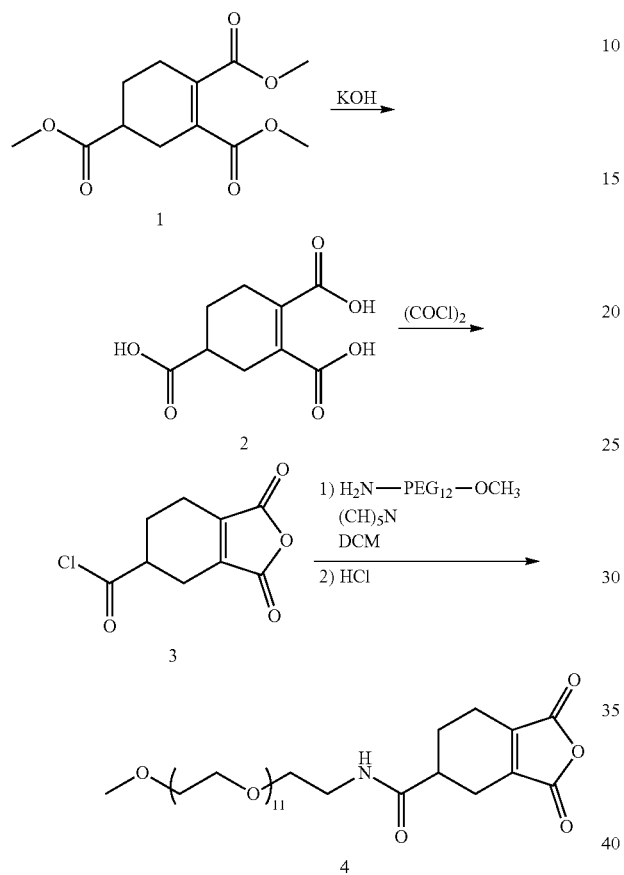

A) 1,2,4-tricarboxy-1-cyclohexene 2. 1,2,4-tricarbomethoxy-1-cyclohexene 1 (465 mg, 1.8 mmol (Claude et al., J. Org. Chem. 2004, 69, 757-764)) was refluxed in a mixture of EtOH (10 mL) and 2N KOH (4 mL) for 1 h. EtOH was removed by rotary evaporation, The residue was diluted with $H_2O$ (20 mL), washed 3 times with DCM, acidified to pH=1 with 10% HCl and product 2 was extracted with EtOAc. The extract was dried using $Na_2SO_4$ as a drying agent, concentrated, and dried in vacuo. Yield 296 mg (73%). $^1$H-NMR (DMSO-$d_6$): 1.6-1.64 m (1H); 1.87-2.00 m (1H); 2.20-2.40 m (5H); 2.42-2.60 m (1H).

B) CycHex-CDM-Cl 3. Triacid 2 (50 mg, 0.234 mmol) was suspended in dichloroethane (10 mL), treated with oxalyl chloride (0.3 mL, 3.4 mmol), and stirred for 24 h at 20° C. All volatiles were removed by rotary evaporation at 25° C. and the residue was dried in vacuo for 4 h.

C) CycHex-CDM-$PEG_{12}$ 4. At 0° C., a solution of $PEG_{12}$ amine (112 mg, 0.2 mmol) and pyridine (92 µL, 1.17 mmol) in DCM (3 mL) was added dropwise into a stirred suspension of CycHex-CDM-Cl 3 (0.234 mmol) in DCM (5 mL). After 20 min at 0° C., the stirring was continued at 20° C. for 16 h. The solvent was removed by rotary evaporation and product 4 was purified by HPLC. Column: Gemini (Phenomenex) 5 µm, C-18, 110 Å, 250×21.2 mm. Mobile phase $CH_3CN$:$H_2O$ ($HCO_2H$ 0.1%), $CH_3CN$ gradient; 15-35% (30 min). Product was concentrated in vacuo, redissolved in $H_2O$ and freeze-dried. Yield 10 mg. MS (ES): 756.5 $[M+H]^+$, 773.6 $[M+NH_4]^+$.

Example 2

Benzo-CDM Derivatives

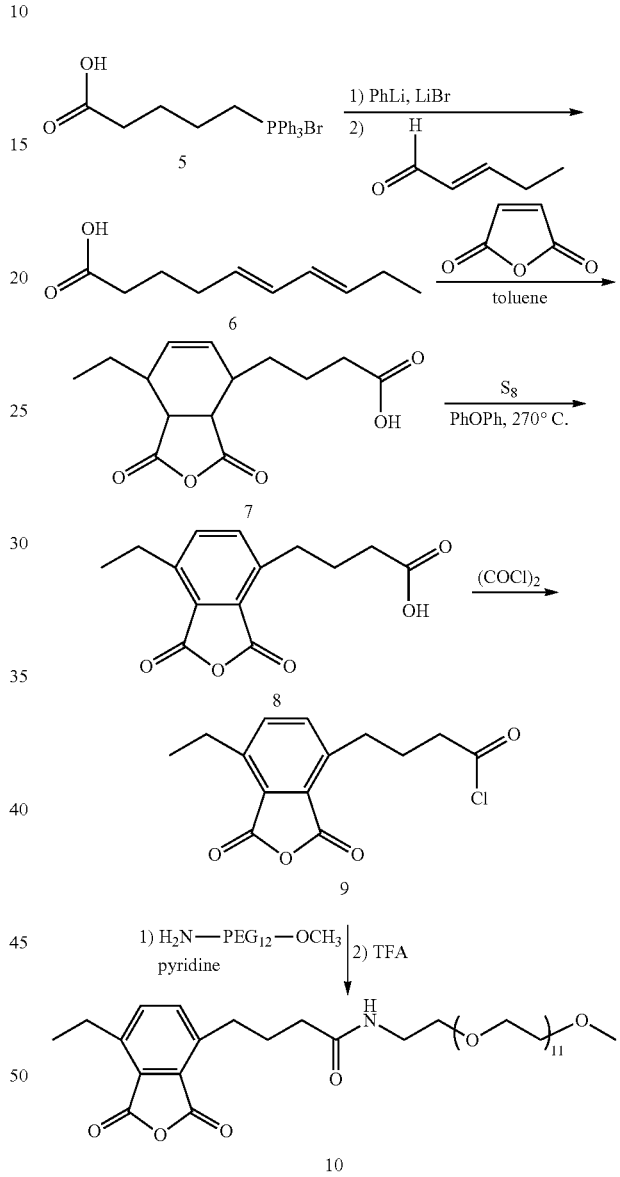

A) (5E,7E)-5, 7-undecandienoic acid 6. LiBr (1.5 M, 56 mL, 84 mmol) was added to a solution of (4-carboxybutyl) triphenylphosphonium bromide 5 (11.08 g, 25 mmol) in THF (45 mL) and cooled to −75° C. While stirring, PhLi (1.8 M in dibutyl ether, 31 mL, 55 mmol) was added dropwise, keeping the temperature of the reaction mixture between −75° C. and −70° C. The cooling bath was removed and the reaction mixture was gradually warmed over 30 min to 25° C. The solution was then cooled to −75° C. and (2E)-2-pentenal (2.103 g, 25 mmol) was added via syringe. The reaction mixture was stirred for 5 min at −75° C. and PhLi (15 mL, 27 mmol) was added over a period of 30 min. The reaction mixture was then stirred for 30 min at −75° C., warmed to 25° C. for 30 min, and then cooled again to −75° C. Hydrogen chloride (1M solution in Et$_2$O, 28 mL, 28 mmol) was added. After 5 min, t-BuOK (3.36 g, 30 mmol) was added. The reaction mixture was allowed to warm to 25° C., stirred for 1 h, and poured into ice cold water (90 mL). The reaction mixture was concentrated twice by rotary evaporation. Unreacted aldehyde was extracted with Et$_2$O. The aqueous layer was acidified to pH=1 with 20% HCl, the product was extracted with Et$_2$O, dried (MgSO$_4$), and purified in a SiO$_2$ column (Hex:EtOAc:AcOH=8:2:0.05). Yield 1.342 g (32%). $^1$H-NMR (CDCl$_3$): 1.00 t (3H, CH$_3$); 1.70 m (2H, CH$_2$); 2.05-2.15 m (4H, 2CH$_2$); 2.36 t (2H, CH$_2$); 5.48-5.57 m (1H, CH); 5.60-5.67 m (1H, CH); 5.96-6.06 m (2H, 2CH). MS (ES, Neg); 166.9 [M−1]$^-$; 395.6 [2M+AcOH−1]$^-$.

B) 4-[17-ethyl-4,7,8,9-tetrahydro-benzo[c]firan-1,3-dione]butyric acid 7. A mixture of acid 6 (1.21 g, 7.2 mmol) and maleic anhydride (741 mg, 7.56 mmol) in toluene (60 mL) was refluxed for 8 h. The Diels-Alder adduct product was concentrated in vacuo and purified on a SiO$_2$ column (Hex:EtOAc:AcOH=7:3:0.05). Yield 1.03 g (53%)$^1$H-NMR (CDCl$_3$): 1.08 t, (3H, CH$_3$); 1.76-1.98 m (6H, 3CH$_2$); 2.12-2.21 m (1H); 2.24-2.32 m (1H, CH); 2.42-2.52 m (2H, CH$_2$); 3.36-3.44 m (2H, CH$_2$); 5.80-5.90 m (2H, 2CH). MS (ES, neg): 265.2 [M−1]$^-$; 531.4 [2M−1]$^-$.

C) 5-(3-Carboxypropyl)-2-ethyl-phthalic anhydride (benzo-CDM) 8. A mixture of adduct 7 (0.5 g, 1.88 mmol) and sulfur (120 mg, 3.76 mmol) in diphenyl ether (3.5 mL) was heated under Argon with stirring on a sand bath at 270° C. for 3.5 h. The reaction mixture was cooled and triturated with hexane. The product was separated by centrifugation and purified on a SiO$_2$ column (AcOH. 0.5% solution in CHCl$_3$). Yield 273 mg (56%): $^1$H-NMR (CDCl$_3$): 1.30 t (3H, CH$_3$); 1.98-2.06 m (2H, CH$_2$); 2.45 t (2H, CH$_2$); 3.07-3.15 m (4H, 2 CH$_2$); 7.59 s (2H, CH). MS (ES, neg): 261.3 [M−1]$^-$; 523.6 [2M−1]$^-$.

D) Benzo-CDM-NH-PEG-OCH$_3$ (Benzo-CDM-PEG) 10. Benzo-CDM 8 (56 mg, 0.214 mmol) was suspended in anhydrous DCM (5 mL) by water bath sonication. Oxalyl chloride (93 µL, 1 mmol) was added, stirred for 20 h, and all volatiles were removed by rotary evaporation at 25° C. The benzo-CDM-COCl 9 was dried in vacuo for 4 h and redissolved in anhydrous DCM (3 mL). CH$_3$O-PEG$_{12}$-NH$_2$ (100 mg, 0.178 mmol) was dried of residual water by addition of anhydrous 1,4-dioxane followed by rotary evaporation. Drying by azeotropic distillation was repeated 3× and finally high vacuum was applied for 3 h. Dry PEG-amine was dissolved in anhydrous DCM (2 mL) along with anhydrous pyridine (84.5 µL, 1.07 mmol). This solution was added dropwise into a stirring solution of benzo-CDM-COCl 9 at 0° C. After 30 min, the cooling bath was removed, and the solution was stirred for 8 h at 20° C. Product benzo-CDM-PEG 10 was concentrated in vacuo and purified on HPLC. Column Aquasil (Thermo), 5 µm, C-18, 250×21.2 mm. Mobile phase: H$_2$O—CH$_3$CN (0.01% TFA) CH$_3$CN gradient; 30-52%, 35 min. Product was concentrated in vacuo, redissolved in H$_2$O and freeze-dried. Yield 40 mg. $^1$H-NMR (CDCl$_3$): 3.30 t (3H, CH$_3$); 1.95-1.21 m (2H, CH$_2$); 2.29 t (2H, CH$_2$CO); 3.06-3.13 m (4H, 2CH$_2$Ph); 3.39 s (3H, CH$_3$); 3.42-3.47 m (2H, CH$_2$); 3.54-3.72 m (46H, PEG); 7.58 d (1H, J=7.9 Hz); 7.62 d (1H, J=7.9 Hz, Ar). MS (ES); 804.6 [M+1]$^+$; 822.5 [M+H$_2$O+1]$^+$; 288.2 [Benzo-CDM-NH—CH=CH$_2$+1]$^+$.

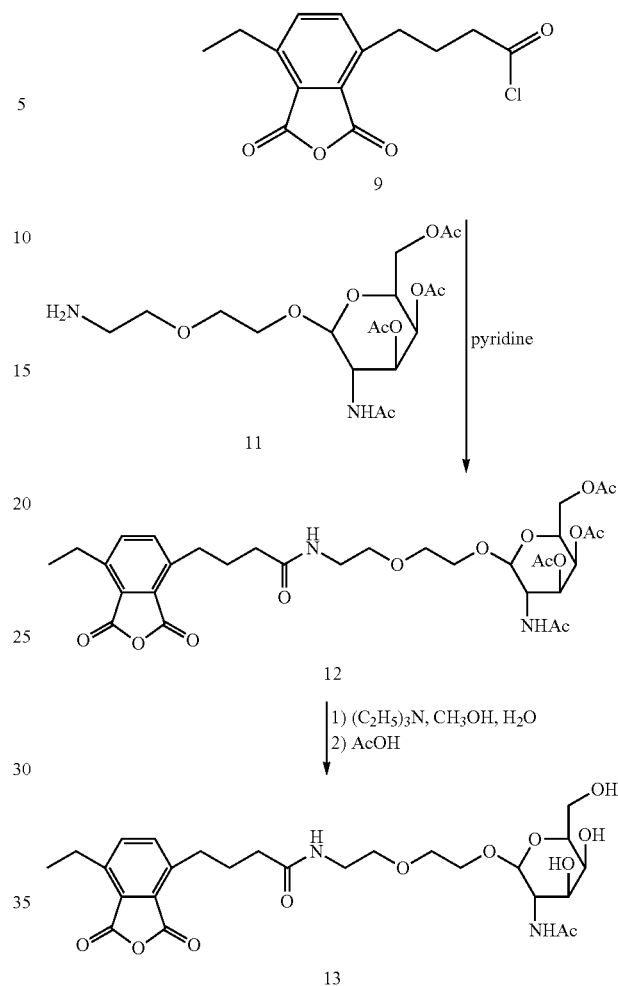

E) Benzo-CDM-NH-NAG 13. Benzo-CDM 8 (100 mg, 0.38 mmol) was converted into benzo-CDM-COCl 9 as described above, and dissolved in anhydrous DCM (4 mL). Ac$_3$-NAG-PEG-amine 11 (0.163 mg, 0.347 mmol) was dried of residual water by addition of anhydrous 1,4-dioxane followed by rotary evaporation. Drying by azeotropic distillation was repeated 3 times, followed by drying in high vacuum for 3 h. Dry material was dissolved in anhydrous DCM (4 mL) containing anhydrous pyridine (150 µL, 1.9 mmol). This solution was added dropwise into a stirring solution of benzo-CDM-COCl 9 at 0° C. After 30 min, the cooling bath was removed and the stirring was continued for 20 h at 20° C. All volatiles were removed by rotary evaporation and dried in vacuo. The residue was dissolved in CHCl$_3$ (75 mL), washed with cold 5% HCl, H$_2$O, and dried with Na$_2$SO$_4$. Column purification on SiO$_2$ (CHCl$_3$:EtOAc: AcOH=4:5:5:0.1) afforded acetyl-protected benzo-CDM-NAG 12, yield 74 mg (31%). The product was stirred in a mixture of MeOH (3 mL): H$_2$O (2 mL): Et$_3$N (2 mL) for 20 h, concentrated in vacuo, redissolved in MeOH (8 mL) and stirred with activated charcoal (3 mg) for 30 min. Following filtration and concentration in vacuo, the product, benzo-CDM-NAG 13, was passed through a Dowex-50WX8-200 (1.5 mL) column (eluent=MeOH: H$_2$O=2:1). This treatment removed Et$_3$N from the product and converts it in to anhydride form due to acidity of released free AcOH. This product was dried in vacuo, redissolved in H$_2$O, and freeze-dried. Yield 40 mg (66%). $^1$H-NMR (D$_2$O, NaHCO$_3$, pH=8.5, different conformations): 1.12-1.20 m (3H, CH$_3$); 1.80-1.92 m (2H, CH$_2$); 2.03 and 2.04 2 s (3H, Ac); 2.22-2.32 m (2H, CH$_2$); 2.60-2.76 (m 4H, 2CH$_2$-Ph); 3.32-3.41 m (2H, CH$_2$N); 3.56-4.04 m (12H, NAG-OCH$_2$CH$_2$OCH$_2$); 4.44 and 4.46 2 d (1H, C$^1$—H galactose), 7.10-7.40 m (2H, Ar). MS (ES); 553 [M+1]$^+$; 585.4 [M+MeOH+1]$^+$. MS (ES, neg): 551 [M−1]$^-$; 569 [M+H$_2$O−1]$^-$; 583 [M+MeOH−1]$^-$.

Example 3

(Meta-Ar)-CDM Derivatives

B) 3-Carboxymethylbenzoic Acid 16. Methyl 3-(cyanomethyl)benzoate 15 (6.3 g, 36.0 mmol) was treated with H$_2$SO$_4$ (40%, 108 mL) and refluxed for 3 h at 160° C. The reaction mixture was then slowly cooled, diluted with cold H$_2$O (108 mL), and filtered. The solid collected was washed with cold H$_2$O, dried with vacuum pump, and used without further purification. Yield 4.4 g (68%). $^1$H-NMR (DMSO): 3.67 s (2H, CH$_2$); 7.44 t (1H, CH), 7.51 dt (1H, CH), 7.82 dt (1H, CH), 7.85 t (1H, CH).

C) Meta-Ar-CDM-CO$_2$H 17. A stirring solution of acetic anhydride (66 mL) containing 3-carboxymethylbenzoic acid 16 (4.4 g, 24.5 mmol) and potassium pyruvate (3.08 g, 24.5 mmol) was heated at 120° C. for 20 min and then concentrated in vacuo. Excess of acetic anhydride was removed by

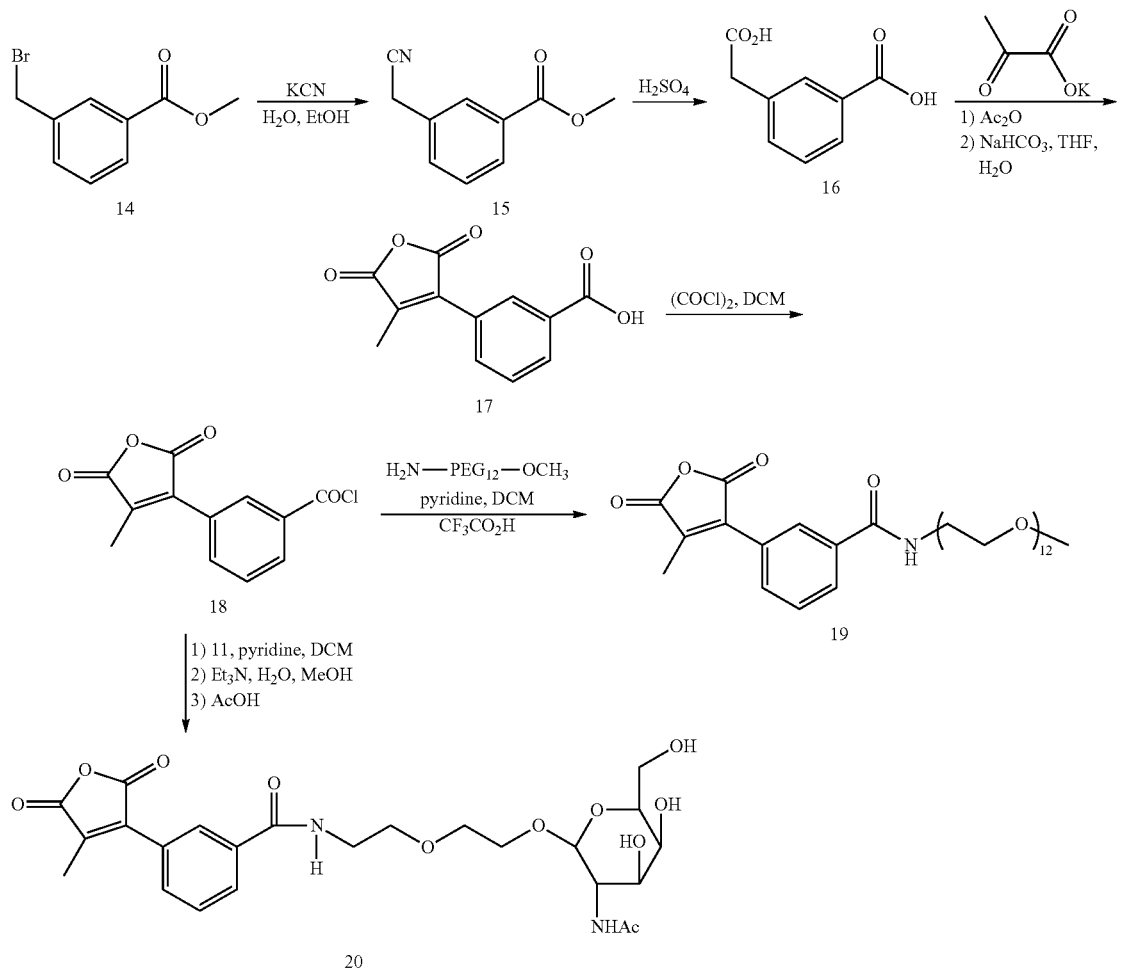

A). Methyl 3-(cyanomethyl)benzoate 15. To a stirring aqueous solution (60 mL) of potassium cyanide (3.62 g, 55.7 mmol) at 65° C. was added dropwise methyl 3-(bromomethyl)benzoate 14 (10.2 g, 44.5 mmol) in absolute ethanol (50 mL) over a period of 0.5 h. After addition, the reaction was stirred for 1.5 h at 65° C. The solution was then diluted with absolute ethanol (500 mL), cooled on ice bath, filtered, and concentrated with a rotary evaporator. The crude was treated with chloroform (350 mL), dried over MgSO$_4$, filtered, concentrated, and used without further purification. Yield 6.3 g (81%). $^1$H-NMR (CDCl$_3$): 3.81 br s (2H, CH$_2$), 3.93 s (3H, CH$_3$); 7.45-7.51 m (1H, CH), 7.53-7.58 m (1H, CH), 7.99-8.04 m (2H, CH).

successive evaporation of toluene from the reaction mixture with a rotary evaporator (3×50 mL). The crude was treated with THF (36 mL) and H$_2$O (30 mL), followed by saturation with NaHCO$_3$, and then stirred at 20° C. for 17 h. The reaction was then diluted with H$_2$O (66 mL), and THF was removed by rotary evaporation. The suspension was washed with DCM (2×50 mL), and the aqueous was acidified to a pH of 1 with 1% HCl. The product was extracted with ethyl acetate (3×200 mL), and the combined organics were washed with brine (2×75 mL), dried with Na$_2$SO$_4$, filtered, and concentrated. The crude was purified by silica gel flash chromatography. Mobile Phase: Hexanes-Ethyl Acetate (H$_3$CCO$_2$H 0.5%), 30-70. Yield 2.87 g (51%). $^1$H-NMR (DMSO): 2.20 s (3H, CH$_3$); 7.70 t (1H, CH), 7.87 dt (1H, CH), 8.09 dt (1H, CH), 8.20 t (1H, CH).

D) Meta-Ar-CDM-PEG$_{12}$ 19. A solution of Meta-Ar 17 (0.25 g, 1.07 mmol) in DCM (30 mL) was treated with oxalyl chloride (0.47 mL, 5.35 mmol) and stirred for 17 h at 20° C. The reaction was concentrated and excess oxalyl chloride removed with vacuum pump. To the resulting solid meta-Ar-CDM-COCl 18 was added DCM (25 mL). The solution was cooled to 0° C., treated dropwise with a mixture of dry CH$_3$O-PEG$_{12}$-NH$_2$ (0.43 g, 0.76 mmol) and pyridine (0.35 mL, 4.28 mmol) in DCM (10 mL), and stirred for 30 min. The ice bath was removed and the mixture was allowed to stir for 17 h at 20° C. The reaction was then concentrated in vacuo, and the crude purified with HPLC. Column: Aquasil (Thermo Scientific) 5 μm, C-18, 100 Å. Mobile phase: H$_2$O-Acetonitrile (F$_3$CO$_2$H 0.01%), Acetonitrile gradient: 33-40%, 35 min. The product 19, Meta-Aromatic-CDM-PEG$_{12}$, collected was then lyophilized from H$_2$O. Yield 97.1 mg (17%). $^1$H-NMR (CDCl$_3$): 2.35 s (3H, CH$_3$); 3.38 s (3H, OCH$_3$), 3.52-3.73 m (48H, CH$_2$); 7.60 t (1H, CH), 7.79 d (1H, CH), 7.97 d (1H, CH), 8.13 s (1H, CH). MS (ES): 258.3 [M−517+1], 517.4 [M−258+1]$^+$; 730.5 [M−44+1]$^+$; 774.5 [M+1]$^+$; 791.9 [M+18]$^+$; 809.7 [M+18+18]$^+$.

E) Meta-Ar-CDM-NAG 20. A solution of m-ArCDM-OH 17 (0.10 g, 0.43 mmol) in DCM (10 mL) was treated with oxalyl chloride (0.19 mL, 2.15 mmol), and concentrated to a solid as described in the preparation of 19. To the resulting solid 18 was added DCM (10 mL). The suspension was cooled to 0° C., treated dropwise with a mixture of dry Ac$_3$-NAG-amine 11 (0.19 g, 0.43 mmol) and pyridine (0.14 mL, 1.72 mmol) in DCM (5 mL), and stirred for 30 min. The ice bath was removed and the mixture was allowed to stir for 17 h at 20° C. The reaction was then concentrated on rotary evaporator and rest of the solvent removed with vacuum pump. The resulting crude was treated with a mixture of methanol (3 mL), H$_2$O (2 mL), and triethyl amine (2 mL). The solution was stirred for 17 h at 20° C., then concentrated with rotary evaporator, and the crude Meta-Ar-CDM-NAG 20 purified with HPLC. Column: Aquasil (Thermo Scientific) 5 μm, C-18, 100 Å. Mobile phase: H$_2$O-MeOH (NH$_4$HCO$_2$ 20 mM), MeOH gradient: 0-10%, 30 min. The solid collected was then passed through Dowex resin (22 mL, 50 W×8-200) using H$_2$O and MeOH as eluent (MeOH gradient: 30-50%). This treatment removed Et$_3$N from the product and converts it in to anhydride form due to acidity of released free HCO$_2$H. The product was then lyophilized from H$_2$O. Yield 28.3 mg (13%). $^1$H-NMR (D$_2$O, NaHCO$_3$): 1.75 s (3H, CH$_3$), 2.01 s (3, CH$_3$); 3.54-4.04 m (14H), 4.49 d (1H, CH); 7.49 dt (1H, CH), 7.55 t (1H, CH), 7.63 t (1H, CH), 7.73 dt (1H, CH). MS (ES): 318.4 [M−204]$^-$; 477.4 [M−44−1]$^-$; 495.8 [M+18−44−1]$^-$; 521.7 [M−1]$^-$; 539.5 [M+18−1]$^-$; 557.4 [M+18+18−1]$^-$; 589.5 [M+18+18+32−1]$^-$.

Example 4

Methoxy-(MeO)-CDM Derivatives

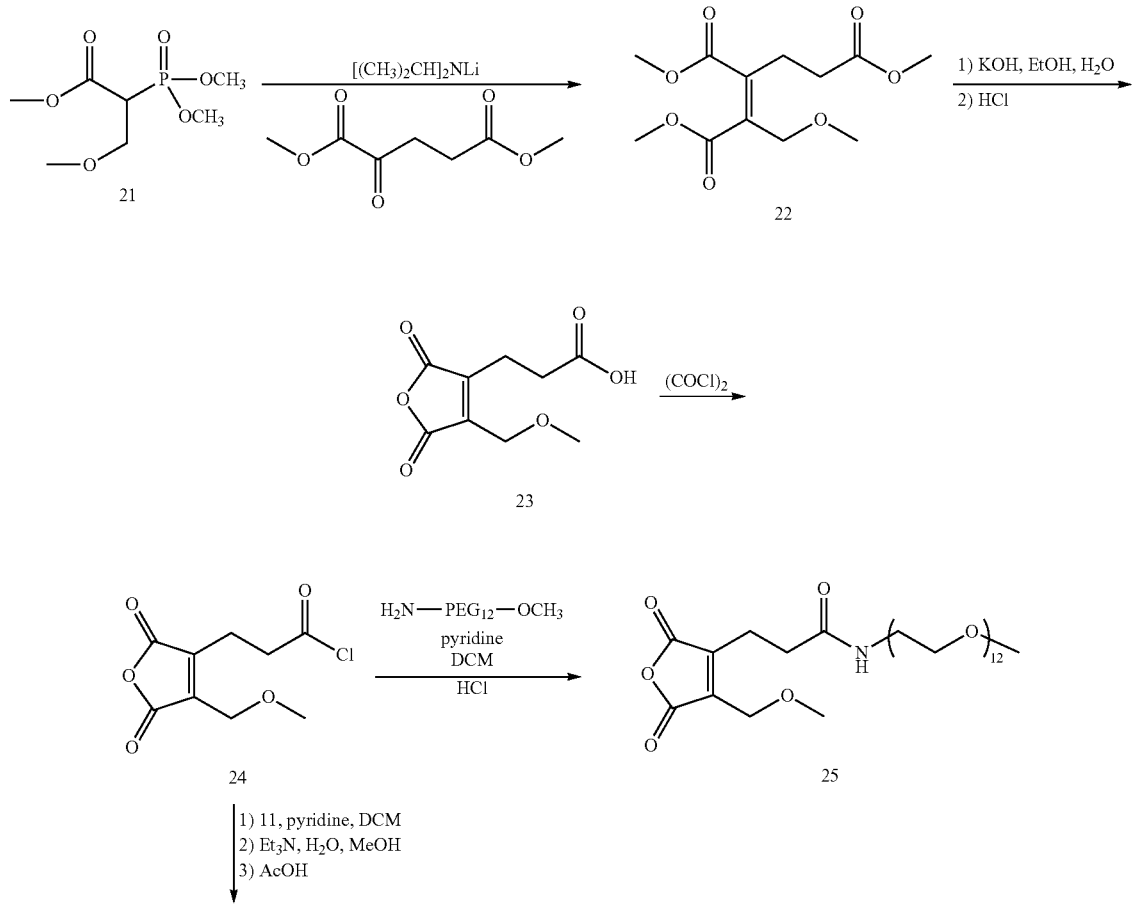

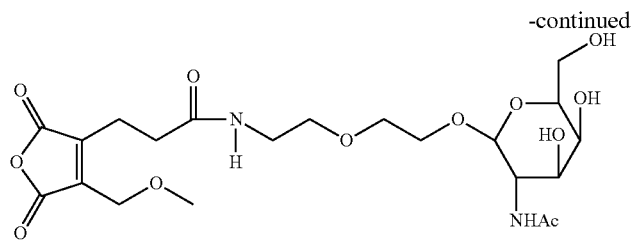

26

A) Methyl 3,5-Dicarbomethoxy-2,3-dehydro-2-methoxymethylpentanoate 22. A solution of diisopropyl amine (1.007 g, 10 mmol) in anhydrous THF (40 mL) was cooled to −40° C. under Argon. Butyl lithium (BuLi, 1.6 M in hexane, 6.2 mL, 9.92 mmol) was added and the reaction stirred from 15 min at −40° C. Trimethyl 3-methoxyl-2-phosphonopropionate 21 (Leonard et al. Synthesis 2000, Vol. 4, 507-509) (2.5 g, 11.06 mmol,) in THF (5 mL) was added dropwise to the obtained lithium diisopropylamide and stirred for 20 min at −40° C. The formed ylide was treated with a solution of dimethyl 2-oxogluterate (1.541 g, 8.85 mmol) in THF (5 mL), stirred for 20 min at −40° C. The temperature was raised, over 1.5 h, to −25° C. The reaction was quenched with saturated solution of $NH_4Cl$ (100 mL). The product was extracted 4× with $Et_2O$, and washed 2× with $KHSO_4$ (5%), then brine. The aqueous layer was extracted once with $Et_2O$. Combined $Et_2O$ extracts were dried ($Na_2SO_4$) and concentrated in vacuo. Product was purified on $SiO_2$ column (33% EtOAc in hexane), yield 1.38 g (56%). $^1$H-NMR ($CDCl_3$): 2.50 t (2H); 2.75 t (2H); 3.36 s (3H), 3.68 s ($CH_3O$); 3.77 s ($CH_3O$), 3.78 s ($CH_3O$); 4.26 s (2H, $\underline{CH_2}OCH_3$) (MS (ES): 297 [M+Na]$^+$; 275.1 [M+1]$^+$; 243.1 [M−$CH_3OH$+1]$^+$.

B) $CH_3O$-CDM-$CO_2H$ 23. Triester 22 (1.281 g, 5 mmol) was dissolved in EtOH (35 mL), 2N KOH (11.3 mL) was added and the reaction mixture was refluxed for 1 h. The solution was diluted with $H_2O$ (15 mL) and EtOH was removed on by rotary evaporation. The residue was washed 3× times with DCM and acidified to pH=1 with 5% HCl. The product was extracted 4× with EtOAc, dried ($Na_2SO_4$), and concentrated in vacuo. Yield 806 mg (75%). $^1$H-NMR ($CDCl_3$): 2.77 t (2H, $CH_2$); 2.94 t (2H, $CH_2$), 3.45 s (3H, $CH_3$); 4.40 s (2H, $CH_2$). MS (ES, Neg.): 231 [M+18−1]$^-$; 199.3 [M−$CH_3OH$−1]$^-$.

C) MeO-CDM-NH-$PEG_{12}$-$OCH_3$ 25. Oxalyl chloride (436 μL, 5 mmol) was added into a solution of MeO-CDM 23 (212 mg, 1 mmol) in DCM (5 mL) and stirred for 20 h at 20° C. The solvent was removed by rotary evaporation at 25° C. and dried under vacuum for 4 h. The resulting MeO-CDM-COCl 24 was dissolved in anhydrous DCM (4 mL) and cooled on an ice bath to 0° C. $CH_3O$-$PEG_{12}$-$NH_2$ (430 mg, 0.769 mmol) in toluene was dried by rotary evaporation of toluene (3×10 mL). The dried $PEG_{12}$ was dissolved in DCM (4 mL), pyridine (360 μL, 4.5 mmol) was added, and the resulting solution was added dropwise into cold stirring solution of MeO-CDM-COCl 24. After 30 min, the cooling bath was removed and the reaction mixture was stirred for 20 h at 20° C. The solution was then diluted with DCM (50 mL). Product was washed with 1% HCl, brine, dried ($Na_2SO_4$) and concentrated in vacuo, and purified on HPLC. Column: Gemini (Phenomenex) 5 μm, C-18, 110 Å, 250×21.2 mm. Mobile phase: $H_2O$—$CH_3CN$ ($HCO_2H$ 0.1%), $CH_3CN$ gradient: 17-35%, 35 min. Product was concentrated in vacuo, redissolved in $H_2O$ and freeze-dried. Yield 100 mg (18%). $^1$H-NMR ($CDCl_3$): 2.58 t (2H, $CH_2$), 2.92 t (2H, $CH_2$); 3.38 s (3H, $CH_3O$); 3.42 t (2H, $CH_2$), 3.44 s (3H, $CH_3O$) 3.52-3.58 m (4H, 2 $CH_2$); 3.60-3.70 m (44H, 22$CH_2$); 4.39 s (2H, $CH_2O$)., 6.6 s (1H, NH). MS (ES): 756.7 [M+1]$^+$, 773.4 [M+18]$^+$.

D) MeO-CDM-O-$PEG_{550}$-$OCH_3$. MeO-CDM-$CO_2H$ 23 (200 mg, 0.935 mmol) was converted into MeO-CDM-COCl as described in preparation of 25 and dissolved in 7 mL DCM. MeO-$PEG_{550}$-OH (Sigma, 343 mg, 623 mmol) was dried by rotary evaporation of 1,4-dioxane (3×5 mL). Dry MeO-$PEG_{550}$-OH and pyridine (0.34 mL, 4.2 mmol) were dissolved in anhydrous DCM (5 mL) and added dropwise into a stirring solution of MeO-CDM-COCl 24 at 0° C. After 30 min, the cooling bath was removed and the reaction mixture stirred for 10 h at 20° C. The reaction mixture was diluted with DCM (60 mL) and washed twice with cold 2% HCl. The aqueous layer was washed once with DCM (15 mL). The organic phases were combined, washed with cold brine, dried ($MgSO_4$), filtered, and concentrated in vacuo. The product was dissolved in EtOAc (2 mL) and added dropwise into a stirring cold $Et_2O$ (45 mL). The mixture was placed on dry ice for 10 h. The precipitate was separated on a centrifuge while cold, dissolved in $Et_2O$ (45 mL), and stirred with activated charcoal (100 mg) for 1 h. Following filtration through Celite, the $Et_2O$ solution of the product was chilled on dry ice for 4 h. The precipitate was centrifuged when cold, separated from the $Et_2O$, and redissolved in $Et_2O$ (40 mL). The precipitation was repeated twice, after which the product was dried in vacuo, then dissolved in $H_2O$ (20 mL), and freeze-dried. Yield 197 mg. $^1$H-NMR ($CDCl_3$); 2.74 t (2H, $CH_2$); 2.92 t (2H, $CH_2$); 3.38 s (3H, $CH_3O$); 3.44 s (3H, $CH_3O$); 3.50-3.58 s (2H, $CH_2$); 3.60-3.70 m (54H, 27$CH_2$); 4.12-4.24 t (2H, $CH_2$, $CH_2OCO$); 4.40 s (2H, $CH_2OCH_3$). MS (ES): 704.4, 748.9, 792.9, 836.7, 880.5, 925.3, 968.8 [M+1]$^+$; 241.2 [MeO–CDM–OCH$CH_2$]$^+$.

E) MeO-CDM-NAG 26. MeO-CDM-$CO_2H$ 23 (202 mg, 0.94 mmol) was converted into MeO-CDM-COCl 24 as described in preparation of 25. $Ac_3$-NAG-PEG-$NH_2$ 11 (402 mg, 0.854 mmol) was dried by rotary evaporation of toluene (3×10 mL) and dissolved in DCM (3 mL). Pyridine was added (334 μL, 4.23 mmol) and the solution was added dropwise into a stirring solution of MeO-CDM-COCl 24 in DCM (2 mL) at 0° C. Following 20 h of stirring at 20° C., the reaction mixture was diluted 10× with DCM, washed twice with cold 3% HCl, dried ($Na_2SO_4$), and concentrated in vacuo. The acetyl-protected product was purified on a $SiO_2$ column (eluent:$CHCl_3$; EtOAc:acetone:acetic acid=4:5:5:0.1). To remove acetyl protective groups from NAG, the product was stirred for 20 h in a mixture of $Et_3N$ (4.5 mL), $H_2O$ (6 mL), MeOH (7.5 mL). Activated charcoal (50 mg) was added and the mixture stirred for 1 h. The reaction mixture was then filtered through Celite. Following concentration in vacuo, the product was passed through a Dowex-50 W×8-200 (4 mL) column (eluent=$H_2O$). This treatment removed $Et_3N$ from the product and converts it in to anhydride form due to acidity of released free AcOH. The product was dried in vacuo, redissolved in $H_2O$, and freeze-dried. $^1$H-NMR ($D_2O$/$NaHCO_3$, open form): 2.05 s (3H, Ac); 2.35 t (2H, CH$_2$), 2.62 t (2H, CH$_2$), 3.35 s (3H, CH$_3$O); 3.35-3.40 m (2H, CH$_2$N); 3.6-4.1 m (12H, galactose+3 CH$_2$); 4.2 s (2H, CH$_2$OCH$_3$); 4.5 d (1H, C$^1$—H galactose). MS (ES): 505.3 [M+1]$^+$; 522.7 [M+18]$^+$; 204.3 [NAG]$^+$.

Example 5

Amido-CDM Derivatives

A) Amido-CDM-PEG

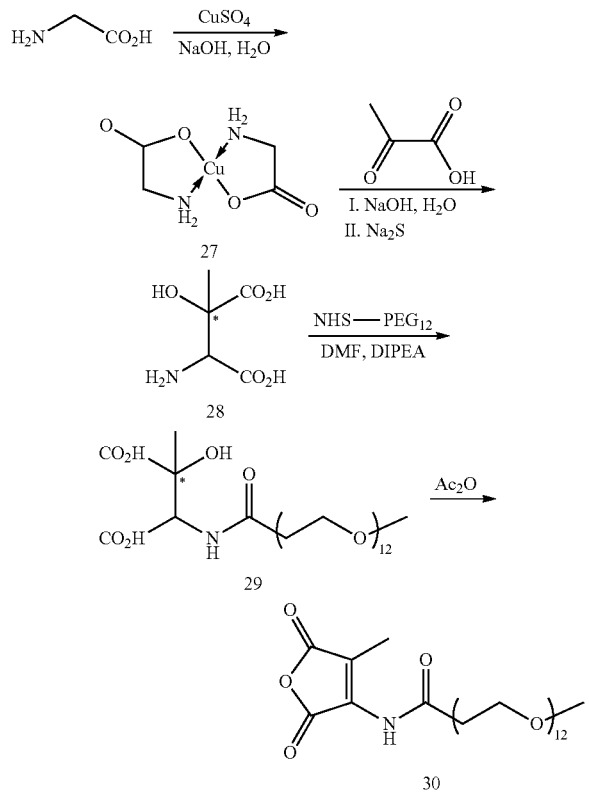

Copper Glycinate 27. Copper glycinate 27 was prepared as described (Sato M, et al. Bulletin of the Chemical Society of Japan 1959, Vol. 32, p. 203-204). An aqueous solution (100 mL) of copper sulfate (7.97 g, 49.9 mmol) and glycine (7.50 g, 99.9 mmol) was treated with sodium hydroxide (3.99 g, 99.9 mmol) and stirred for 30 min at 50° C. The solution was then diluted with cold ethanol (350 mL) and the product collected by filtration. The precipitate was crystallized as fine needles from ethanol (250 mL) in water (350 mL). Yield 10.78 g (87%).

β-Hydroxy-β-methylaspartic Acid 28. β-Hydroxy-β-methylaspartic Acid 28 was prepared using a modified procedure as described (Benoiton L, et al. Journal of the American Chemical Society 1959, Vol. 81, p. 1726-1'729).

To an aqueous solution of sodium hydroxide (0.5 N, 12 mL) containing copper glycinate 27 (0.75 g, 3.02 mmol) was added a solution of pyruvic acid (0.32 g, 3.63 mmol) in H$_2$O (2.5 mL) neutralized with sodium bicarbonate (pH 7). The suspension was stirred for 3 min at 20° C., and then let to stand for 16 h at 5° C. The resulting suspension was filtered and the filtrate treated with sodium sulfide (0.25 g, 3.18 mmol) in H$_2$O (50 mL) for 30 min with stirring at 20° C. The black copper salts were removed by filtration, and the solution concentrated in vacuo. The oily crude was passed through Dowex 1-Acetate (25 mL, 200-400 mesh) and concentrated as a white precipitate (eluent: H$_2$O). The product collected was neutralized with sodium bicarbonate (pH 7) in a minimum of H$_2$O, and loaded onto Dowex 1-Acetate (25 mL, 200-400 mesh). The column was washed with H$_2$O until no more ninhydrin positive material was collected. The resin was removed from the column and stirred in 1 N acetic acid until hydrogen sulfide ceased to form. This was reloaded into the column and the product was flushed using 1 N acetic acid. Yield 0.31 g (63%). (D$_2$O): 1.49 s (3H, CH$_3$), 1.54 s (3H', CH$_3$'); 4.09 s (1H, CH), 4.18 s (1H', CH').

β-PEG$_{12}$-β-methylaspartic Acid 29. A solution containing β-hydroxy-β-methylaspartic acid 28 (95.4 mg, 0.59 mmol) and N,N-diisopropylethylamine (0.31 mL, 1.76 mmol) in DMF (4 mL) was treated with NHS-PEG$_{12}$ (382 mg, 0.56 mmol) and let to stir for 16 h at 20° C. The solution was then concentrated and purified with HPLC, but it may be used without further purification. Column: Gemini (Phenomenex) 5 μm, C-18, 110 Å. Mobile phase: H$_2$O-MeOH (HCO$_2$H 0.1%), MeOH gradient: 36-44%, 35 min. The solution was concentrated and dried using vacuum pump for 24 h. Yield 260 mg (63%). (D$_2$O): 1.36 s (3H, CH$_3$), 1.48 s (3H', CH$_3$'); 2.58-2.75 m (2H, CH$_2$CONH), 3.38 s (3H, OCH$_3$); 3.60-3.73 m (44H, OCH$_2$), 2.83 t (2H, OCH$_2$); 4.67 s (1H', CH), 4.99 s (1H, CH). MS (ES): 716.5 [M−18]$^+$; 734.5 [M+1]$^+$; 751.8 [M+18]$^+$; 772.3 [M+38]$^+$.

Amido-CDM-PEG$_{12}$ 30. Dry β-PEG$_{12}$-β-methylaspartic acid 29 (260 mg, 0.35 mmol) was treated with acetic anhydride (5 mL) freshly distilled from dry sodium acetate and stirred for 15 min at 100° C. The reaction was immediately concentrated with a rotary evaporator, dried by evaporation of toluene from the reaction mixture (3×, 3 mL), and purified by HPLC. Column: Gemini (Phenomenex) 5 μm, C-18, 110 Å. Mobile phase: H$_2$O-MeOH (HCO$_2$H 0.1%), MeOH gradient: 39-55%, 30 min. The product collected was then lyophilized from H$_2$O (0.01% F$_3$CCO$_2$H). Yield 73 mg (30%). $^1$H-NMR (D$_2$O): 2.25 s (3H, CH$_3$), 2.73 t (2H, CH$_2$CONH), 3.38 s (3H, OCH$_3$); 3.56 m (2H, OCH$_2$), 3.59-3.70 m (44H, OCH$_2$); 3.82 s (2H, OCH$_2$). MS (ES): 698.6 [M+1]$^+$; 712.6 [M+32−18]$^+$; 715.4 [M+18]$^+$; 730.5 [M+32]$^+$; 733.6 [M+18+18]$^+$; 747.6 [M+18+32]$^+$.

B) Amido-CDM-N-Acetyl-Galactosamine (Amido-CDM-NAG)

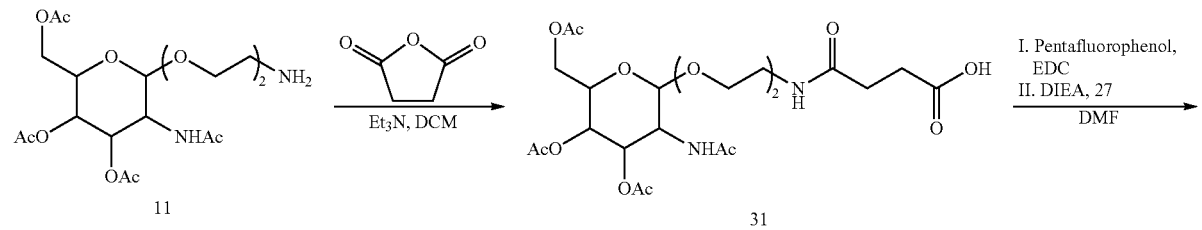

-continued

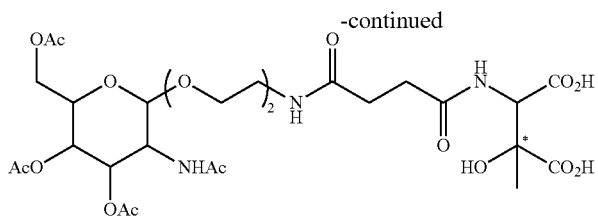
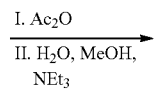

32

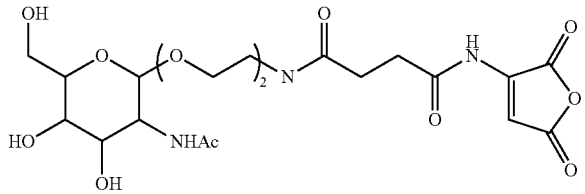

33

N-Acetyl-Galactose-succinate 31. A solution containing N-acetyl-galactose (1.00 g, 2.30 mmol) 11 and succinic anhydride (244 mg, 2.41 mmol) in DCM (22 mL) was treated with triethyl amine (404 µL, 2.9 mmol) and stirred for 1 h at 20° C. The solution was concentrated and the product purified by silica gel flash chromatography. Mobile Phase: $CHCl_3$-MeOH ($H_3CCO_2H$ 1%), 19-1. Yield 1.18 g (96%). $^1$H-NMR (DMSO): 1.78 s (3H, OAc), 1.89 s (3H, OAc), 1.99 s (3H, OAc), 2.10 s (3H, NHAc); 2.32 t (2H, $OCOCH_2$), 2.41 t (2H, $NHCOCH_2$); 3.17 m (2H, $OCH_2$), 3.38 t (2H, $NHCOCH_2$), 3.45-3.62 m (3H, CH; $OCH_2$), 3.75-3.92 m (2H, $OCH_2$) 4.02 br s (3H, CH; $AcOCH_2$); 4.54 d (1H, CH), 4.98 dd (1H, CH), 5.21 d (1H, CH); 7.83 d (1H, NH), 7.89 t (1H, NH). MS (ES): 330.3 [M−205+1]$^+$; 535.5 [M+1]$^+$; 552.5 [M+18]$^+$.

β-N-Acetyl-Galactose-β-methylaspartic acid 32. Dry N-acetyl-galactose-succinate 31 (715 mg, 1.34 mmol) in DMF (15 mL) was treated with pentafluorophenol (320 mg, 1.74 mmol), then EDC (333 mg, 1.74 mmol), and let to stir for 18 h at 20° C. To the solution at 0° C. was then added dropwise a suspension of β-hydroxy-β-methylaspartic acid 28 (283 mg, 1.74 mmol) and N,N-diisopropylethylamine (1.16 mL, 6.68 mmol) in DMF (20 mL). The solution was let to warm to 20° C., and stirred for 18 h. It was then concentrated on a rotary evaporator and purified with HPLC. Column: Aquasil (Thermo Scientific) 5 µm, C-18, 100 Å. Mobile phase: $H_2O$-Acetonitrile ($HCO_2H$ 0.1%), Acetonitrile gradient: 11-19%, 30 min. Yield 342 mg (38%). $^1$H-NMR (DMSO): 1.17 s (3H, $CH_3'$), 1.36 s (3H, $CH_3$), 1.78 s (3H, OAc), 1.89 s (3H, OAc), 1.99 s (3H, OAc), 2.10 s (3H, NHAc); 2.24-2.39 m (4H, $CH_2$); 3.18 t (2H, $CH_2$); 3.38 t (2H, $CH_2$), 3.45-3.63 m (3H, CH; $OCH_2$), 3.75-3.92 m (2H, $OCH_2$) 4.03 br s (3H, CH; $AcOCH_2$); 4.54 d (1H, CH); 4.57 d (1H, CH), 4.89 d 1H, CH'); 4.97 dd (1H, CH), 5.21 d (1H, CH); 7.82 d (1H, NH), 7.87 t (1H, NH). MS (ES): 330.3 [M−360+1]$^+$; 351.4 [M−360+22]$^+$; 690.4 [M+1]$^+$; 702.3 [M+22]$^+$; 718.4 [M+38]$^+$.

Amido-CDM-NAG 33. Amido-CDM-NAG was prepared by treatment of β-N-Acetyl-Galactose-β-methylaspartic acid 32 (342 mg, 0.50 mmol) with freshly distilled acetic anhydride (5 mL) as described in the preparation of 30. The resulting crude was treated with a mixture of methanol (7.5 mL), $H_2O$ (6 mL), and triethyl amine (4.5 mL). The solution was stirred for 17 h at 20° C., then concentrated with a rotary evaporator and purified with HPLC. Column: Aquasil (Thermo Scientific) 5 µm, C-18, 100 Å. Mobile phase: $H_2O$-Acetonitrile ($F_3CCO_2H$ 0.01%), Acetonitrile gradient: 5-25%, 35 min. The product collected was then lyophilized from $H_2O$ (0.01% $F_3CCO_2H$). Yield 50 mg (19%). $^1$H-NMR ($D_2O$, $NaHCO_3$): 1.84 s (3H, $CH_3$), 2.05 s (3H, $CH_3$); 2.54-2.76 m (4H, $CH_2$), 3.36-3.44 m (2H, $CH_2NHCO$); 3.59-4.22 m (12H), 4.5 d (1H, CH). MS (ES): 204.3 [M−314+1]$^+$; 314.9 [M−204+1]$^+$; 333.3 [M−204+18]$^+$; 347.3 [M−204+32]$^+$; 518.6 [M+1]$^+$; 536.6 [M+18]$^+$; 550.6 [M+32]$^+$; 572.4 [M+32+32]$^+$; 588.3 [M+32+38]$^+$.

Example 6

Polymer-siRNA Conjugation

A) Modification of Amino-siRNA with Thioacetyl Group. SATA-modified siRNAs were synthesized by reaction of 5' amine-modified siRNA with 1 weight equivalents (wt. eq.) of N-succinimidyl-S-acetylthioacetate (SATA) reagent (Pierce) and 0.36 wt. eq. of $NaHCO_3$ in water at 4° C. for 16 hours. The modified siRNAs were then precipitated by the addition of 9 volumes of ethanol and incubation at −78° C. for 2 hours. The precipitate was isolated and dissolved in 1×siRNA buffer (Dharmacon), and quantified by measuring absorbance at the 260 nm wavelength.

B. Conjugation of siRNA and Polymer, Followed by Reversible Modification of Polymer. Polymer was modified by addition of 1.5 wt % SMPT (Pierce). One hour after addition of SMPT, the 1×mg of modified polymer was added to isotonic glucose solution. To this solution was added <0.25×mg SATA-modified siRNA. To the solution was then added 14×mg of HEPES free base followed by a mixture of 2.3×mg NAG-containing CDM derivatives and 4.7×mg PEG-modified CDM derivatives. The solution was then incubated 0.5 hour at room temperature before injection.

Example 7

Reversible Polymer Modification

Reversible modification/masking of membrane active polyamine; i.e., modification of membrane active polymer with CDM-NAG or a mixture of CDM-NAG plus CDM-PEG. Masking of polymer: To a solution of xmg membrane active polyamine in isotonic glucose was added 14×mg of HEPES free base followed by either 7×mg CDM-NAG or a mixture of 2.3×mg CDM-NAG and 4.6×mg CDM-PEG, for a total of 7×disubstituted maleic anhydride masking agent. The solution was then incubated for at least 30 min at RT prior to animal administration.

Example 8

In Vivo siRNA Delivery

A) Administration of RNAi Polynucleotides In Vivo and Delivery to Hepatocytes. RNAi polynucleotide and masked polymers conjugates were synthesized as described above. Six to eight week old mice (strain C57BL/6 or ICR, ~18-20 g each) were obtained from Harlan Sprague Dawley (Indianapolis Ind.). Mice were housed at least 2 days prior to injection. Feeding was performed ad libitum with Harlan Teklad Rodent Diet (Harlan, Madison Wis.). Mice were injected with 0.2 mL solution of delivery polymer-siRNA conjugates into the tail vein. The composition was soluble and nonaggregating in physiological conditions. Solutions were injected by infusion into the tail vein. Injection into other vessels, e.g. retro-orbital injection, were equally effective.

B) Serum ApoB Levels Determination. Mice were fasted for 4 h (16 h for rats) before serum collection by submandibular bleeding. Serum ApoB protein levels were determined by standard sandwich ELISA methods. Briefly, a polyclonal goat anti-mouse ApoB antibody and a rabbit anti-mouse ApoB antibody (Biodesign International) were used as capture and detection antibodies respectively. An HRP-conjugated goat anti-rabbit IgG antibody (Sigma) was applied afterwards to bind the ApoB/antibody complex. Absorbance of tetramethyl-benzidine (TMB, Sigma) colorimetric development was then measured by a Tecan Safire2 (Austria, Europe) microplate reader at 450 nm.

C) Plasma Factor VII (F7) Activity Measurements. Plasma samples from mice were prepared by collecting blood (9 volumes) by submandibular bleeding into microcentrifuge tubes containing 0.109 mol/L sodium citrate anticoagulant (1 volume) following standard procedures. F7 activity in plasma is measured with a chromogenic method using a BIOPHEN VII kit (Hyphen BioMed/Aniara, Mason, Ohio) following manufacturer's recommendations. Absorbance of colorimetric development was measured using a Tecan Safire2 microplate reader at 405 nm.

TABLE 1

Knockdown of apoB in vivo following injection of siRNA-polymer[a] conjugate reversibly masked with different CDM derivatives.

| CDM derivative | siRNA dose (mg/kg) | Polymer dose (mg/kg) | Relative % ApoB [b, c] |
|---|---|---|---|
| Standard CDM | 1 | 15 | 96 ± 1 |
| Amido-CDM | 1 | 15 | 94 ± 1 |
| Meta aryl-CDM | 1 | 15 | 95 ± 1 |

[a]Polymer used was PBAVE (U.S. Pat. No. 7,682,626)
[b] Percent knockdown relative to control group (n = 3) injected with isotonic glucose solution.
[c] ICR mice

Example 8 siRNA Delivery by Co-Injection of siRNA-Cholesterol Conjugate and Reversibly Modified Polyamine Six to eight week old mice (strain C57BL/6 or ICR, ~18-20 g each) were obtained from Harlan Sprague Dawley (Indianapolis Ind.). Mice were housed at least 2 days prior to injection. Feeding was performed ad libitum with Harlan Teklad Rodent Diet (Harlan, Madison Wis.). Cholesterol was were covalently linked to 3' or 5' ends of siRNA molecules using techniques standard in the art. Polyamines were reversibly modified as described above. Mice were injected with 0.2 mL solution of delivery polymer and 0.2 mL siRNA conjugates into the tail vein. The composition was soluble and nonaggregating in physiological conditions. Solutions were injected by infusion into the tail vein. Injection into other vessels, e.g. retro-orbital injection, were equally effective.

TABLE 2

Knockdown of apoB in vivo following injection of siRNA-cholesterol conjugate coadministered with reversibly masked with different CDM derivatives.

| CDM derivative | siRNA dose (mg/kg) | Polymer dose[a] (mg/kg) | Relative % ApoB [b, c] |
|---|---|---|---|
| Standard CDM | 1 | 15 | 62 ± 10 |
| methoxy-CDM | 1 | 15 | 67 ± 13 |

[a]Polymer used was PBAVE.
[b] Percent knockdown relative to control group (n = 3) injected with isotonic glucose solution.
[c] ICR mice.

Example 9

Circulation Times for Polymers Modified with Anhydride Derivative PEG Compounds Polyamines were modified with the indicated anhydride derivative-PEG compounds and fluorescently labeled. Following polymer modification, the polymers were injected into mice and the circulation times monitored by fluorescence.

Ant-86 poly(acrylate) polyamine was labeled with Cy5 or Cy7. The labeled polymers were then modified with the indicated anhydride derivative-PEG550 (550 MW PEG) compounds by reaction in HEPES buffered isotonic glucose at pH7.5 at room temperature for 15-30 min. The conjugates were injected into ICR mice (100 µg polymer per mouse in a volume of 200 µL). At several time points after delivery, a small amount of blood was obtained from the mice and immediately placed on ice. The blood samples were subsequently spun in serum separation tubes and the serum transferred to new tubes. The amount of polymer in each sample was determined by measuring the fluorescence intensity of the label in a fluorometer (Cy5 at 650 nm, Cy7 at 670 nm). The data for each individual mouse were normalized by dividing each value by the value of the first data point (typically collected at 2 min after injection to give a measure of the injected amount). Each sample was injected in three mice. The following table provides the average data obtained for various formulations. The data reveal different circulation times for polymers conjugated with different anhydride derivative-PEG compounds.

TABLE 3

In vivo clearance from serum of polymers modified with anhydride-PEG compounds.

| anhydride | Relative amount of polymer remaining in circulation | | | |
|---|---|---|---|---|
| | 2 min* | 30 min | 60 min | 120 min |
| 2-propionic-3-methylmaleic anhydride | 1.00 | 0.31 ± 0.18 | 0.06 ± 0.06 | 0.03 ± 0.03 |
| NHS (non-labile control) | 1.00 | 0.94 ± 0.06 | 0.71 ± 0.12 | 0.63 ± 0.10 |
| Meta-aryl-CDM | 1.00 | 0.61 ± 0.12 | 0.29 ± 0.06 | 0.09 ± 0.03 |
| Amido-CDM | 1.00 | 0.53 ± 0.14 | 0.39 ± 0.17 | 0.40 ± 0.00 |

*Minutes after injection.

We claim:

1. An anhydride comprising the structure represented by:

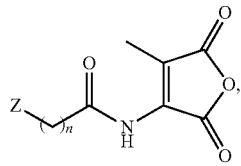

wherein n is an integer from 1 to 8; and
Z comprises a carboxyl group, a hydroxyl group, an ester group, an amide group, an ether group, a tertiary amine group, a protected amine group, a targeting group, or a steric stabilizer group.

2. The anhydride of claim 1, wherein:
Z is selected from the group consisting of: hydroxyl group, targeting group, and steric stabilizer group.

3. The anhydride of claim 1, wherein the targeting group is an N-acetylgalactosamine.

4. The anhydride of claim 1, wherein the steric stabilizer is a polyethyleneglycol.

5. The anhydride of claim 1, wherein Z comprises polyethylene glycol.

6. The anhydride of claim 1, wherein n is 1.

7. The anhydride of claim 1, wherein n is 2.

* * * * *